Figure 1:
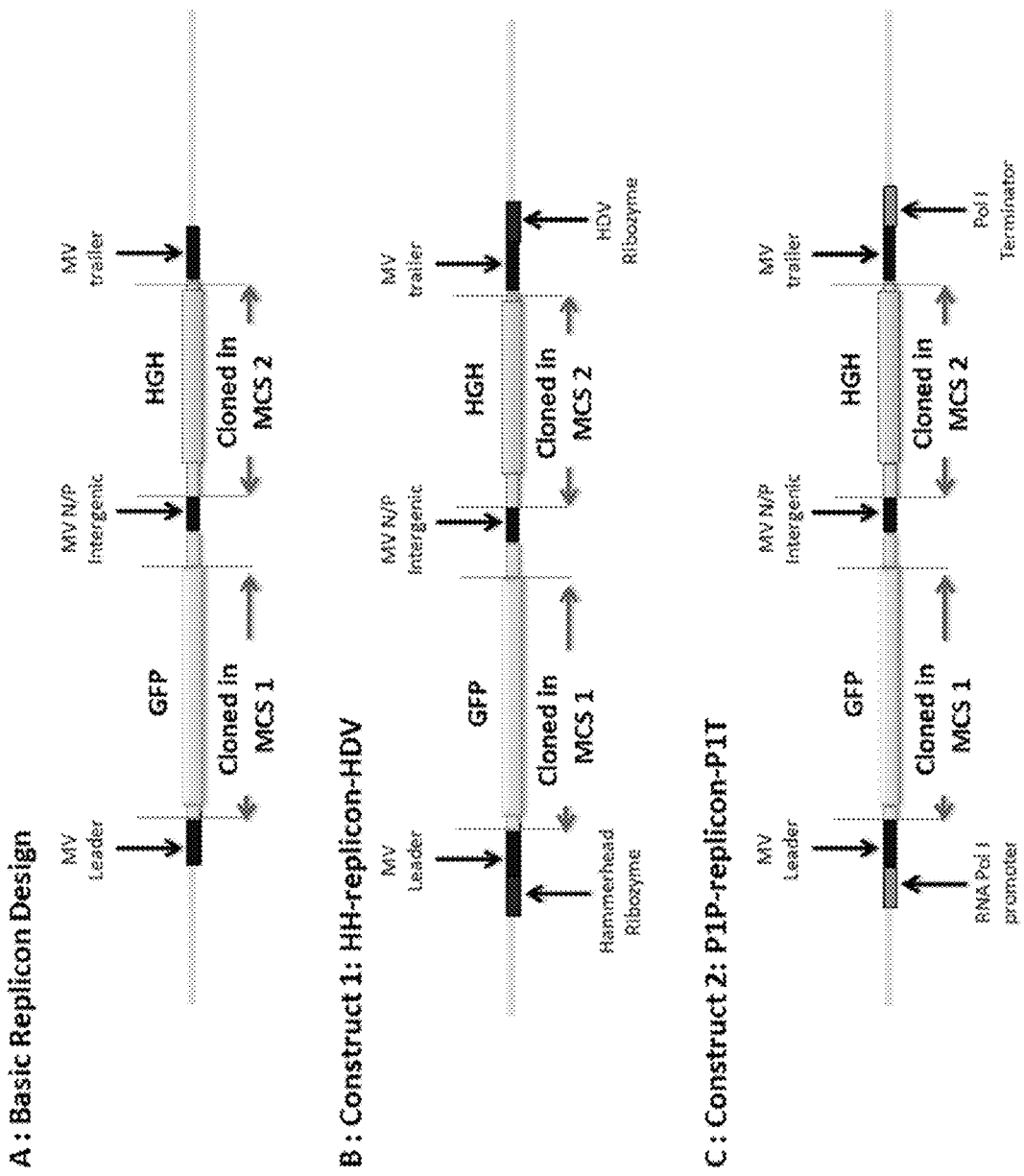

US009441205B2

(12) United States Patent
Joshi

(10) Patent No.: US 9,441,205 B2
(45) Date of Patent: Sep. 13, 2016

(54) TWO PLASMID MAMMALIAN EXPRESSION SYSTEM

(76) Inventor: Vishwas Joshi, Maharashtra (IN)

( * ) Notice: Subject to any disclaimer, the term of this patent is extended or adjusted under 35 U.S.C. 154(b) by 0 days.

(21) Appl. No.: 14/124,383

(22) PCT Filed: Jun. 8, 2012

(86) PCT No.: PCT/IN2012/000405
§ 371 (c)(1), (2), (4) Date: Feb. 27, 2014

(87) PCT Pub. No.: WO2013/046216
PCT Pub. Date: Apr. 4, 2013

(65) Prior Publication Data

US 2014/0212922 A1 Jul. 31, 2014

(30) Foreign Application Priority Data

Jun. 8, 2011 (IN) ......................... 1679/MUM/2011

(51) Int. Cl.
*C12N 15/85* (2006.01)
*C12N 7/00* (2006.01)
*C12N 15/86* (2006.01)

(52) U.S. Cl.
CPC ................. *C12N 7/00* (2013.01); *C12N 15/85* (2013.01); *C12N 15/86* (2013.01); *C12N 2760/00051* (2013.01); *C12N 2760/18451* (2013.01); *C12N 2800/40* (2013.01); *C12N 2840/203* (2013.01)

(58) Field of Classification Search
None
See application file for complete search history.

(56) References Cited

U.S. PATENT DOCUMENTS 5,716,821 A 2/1998 Wertz et al.
2008/0274130 A1 11/2008 Rupprecht et al.
2010/0028377 A1* 2/2010 Jin et al. .................... 424/199.1

FOREIGN PATENT DOCUMENTS

WO WO 97/06270 2/1997
WO WO 98/13501 4/1998
WO WO 00/26517 5/2000
WO WO 2004/113517 A2 12/2004

OTHER PUBLICATIONS

Showronek et al., Analytical Biochemistry, 2002, vol. 300, pp. 185-191.*
Martin et al., Journal of Virology, 2006, vol. 80, pp. 5708-5715.*
Radcliffe et al., GEne Therapy, 2004, vol. 11, pp. 1673-1674.*
International Search Report for PCT/IN2012/000405 mailed Mar. 4, 2013.
Martin et al., "RNA Polymerase II-Controlled Expression of Antigenomic RNA Enhances the Rescue Efficacies of Two Different Members of the *Mononegavirales* Independently of the Site of Viral Genome Replication," Journal of Virology, Jun. 2006, vol. 80, No. 12, 5708-5715.
Groseth et al., "RNA Polymerase I-Driven Minigenome System for Ebola Viruses," Journal of Virology, Apr. 2005, vol. 79, No. 7, 4425-4433.
Yanai et al., "Development of a novel Borna disease virus reverse genetics system using RNA polymerase II promoter and SV40 nuclear import signal," Microbes and Infection 8 (2006) 1522-1529.
Finke et al., "Differential Transcription Attenuation of Rabies Virus Genes by Intergenic Regions: Generation of Recombinant Viruses Overexpressing the Polymerase Gene," Journal of Virology, Aug. 2000, vol. 74, No. 16, 7261-7269.
Szymczak et al., "Development of 2A peptide-based strategies in the design of multicistronic vectors," Expert Opinion Biol. Ther, (2005) 5(5) 627-638.
Szymczak et al., "Correction of multi-gene deficiency in vivo using a single 'self-cleaving' 2A peptide-based retroviral vector," Nature Biotechnology vol. 22, No. 5, May 2004, 589-594.
Huang et al., "Development of a reverse genetics system for a human rabies virus vaccine strain employed in China," Virus Research 149 (2010) 28-35.
Parida et al., "Rescue of a chimeric rinderpest virus with the nucleocapsid protein derived from peste-des-petits-ruminants virus: use as a marker vaccine," Journal of General Virology (2007), 88, 2019-2027.
Bailey et al., "Reverse genetics for peste-des-petits-ruminants virus (PPRV): Promoter and protein specificities," Virus Research 126 (2007) 250-255.
Raha et al., "Development of a reconstitution system for Rinderpest virus RNA synthesis in vitro," Virus Research 99 (2004) 131-138.
Supplementary European Search Report and Written Opinion issued in EP 12 83 5226 dated Jan. 14, 2015.

* cited by examiner

*Primary Examiner* — Michele K Joike
*Assistant Examiner* — Mindy G Brown
(74) *Attorney, Agent, or Firm* — RatnerPrestia

(57) ABSTRACT

Reverse engineering has offered new ways of studying the pathology of RNA viral infections, new more efficient devices of synthesizing recombinant viruses and developing vaccines and also demonstrated the versatility and efficiency of RNA dependent RNA polymerase RDRP system as an expression system. However, the currently used methods require a repertoire of complex, difficult-to-use tools. Present invention describes, a simpler plasmid based mammalian expression system that uses the RDRP enzyme activity for expression of recombinant proteins or RNA from viral minigenomes and rescue of recombinant viruses from cDNAs encoding entire genome(s) of negative stranded RNA viruses. This system will be useful for expression of recombinant proteins, therapeutic RNA molecules including anti-sense and/or selecting interfering RNA and Ribozymes. This system can also be used for gene therapy and producing recombinant viruses for production of new vaccines.

9 Claims, 16 Drawing Sheets

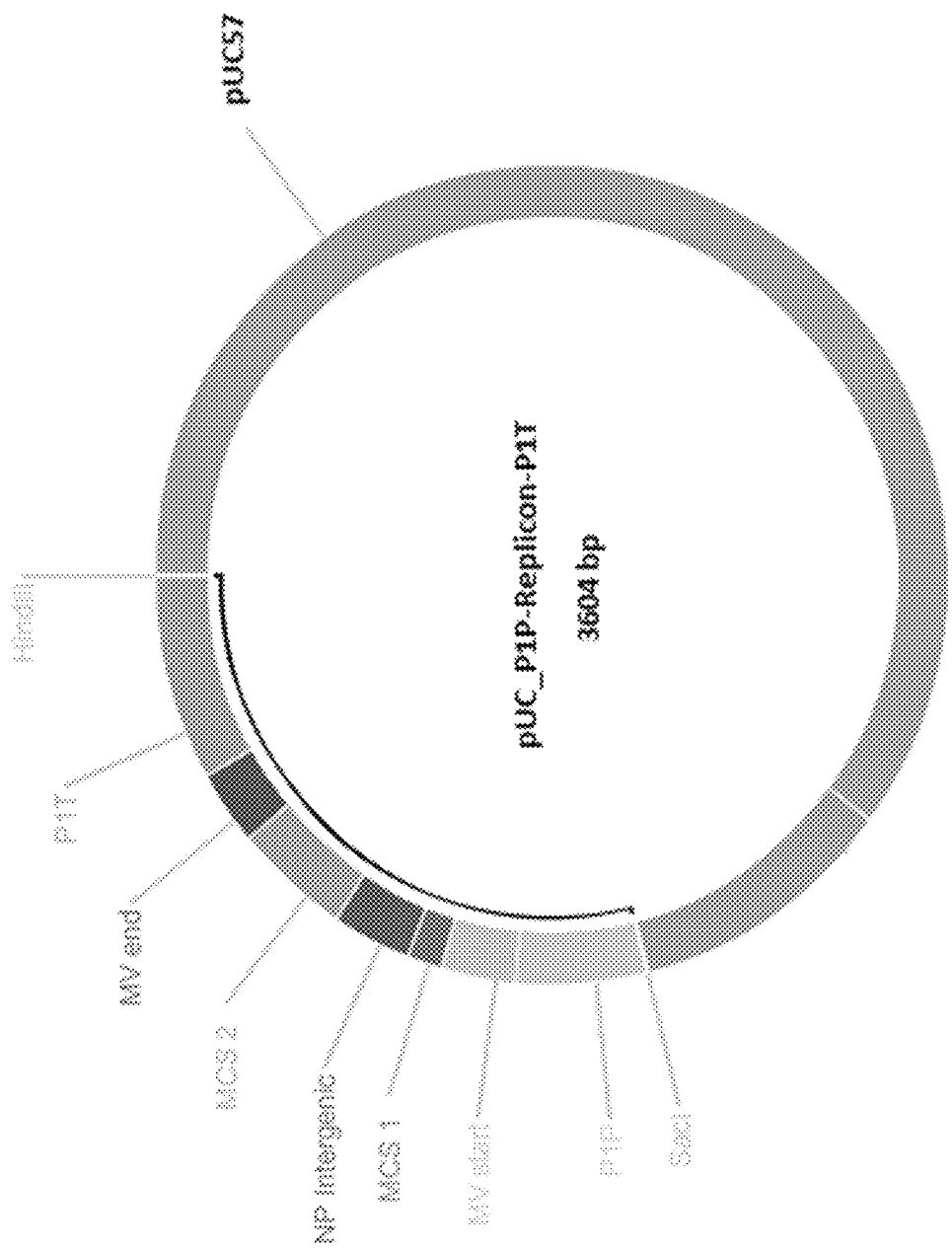
Fig 2A cloning plasmid 1

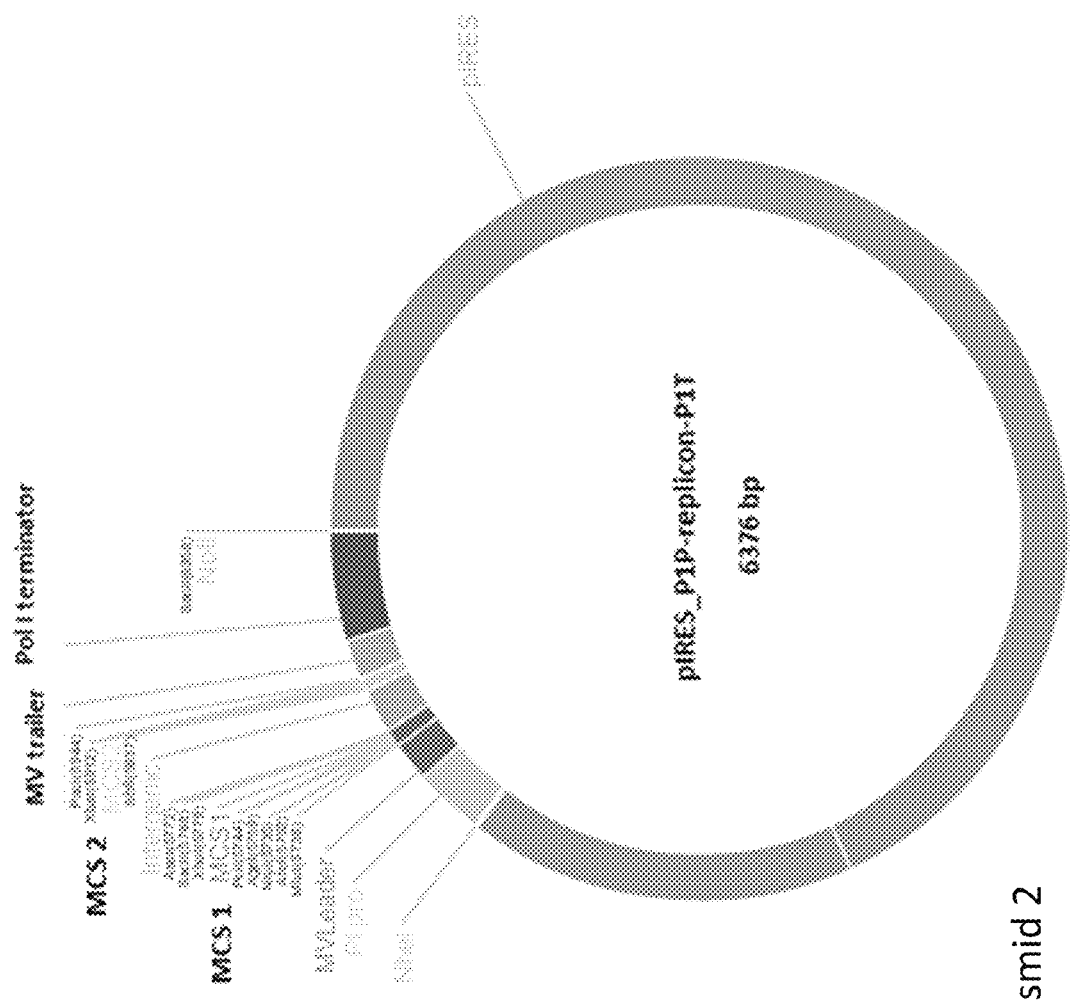
Fig 2B cloning plasmid 2

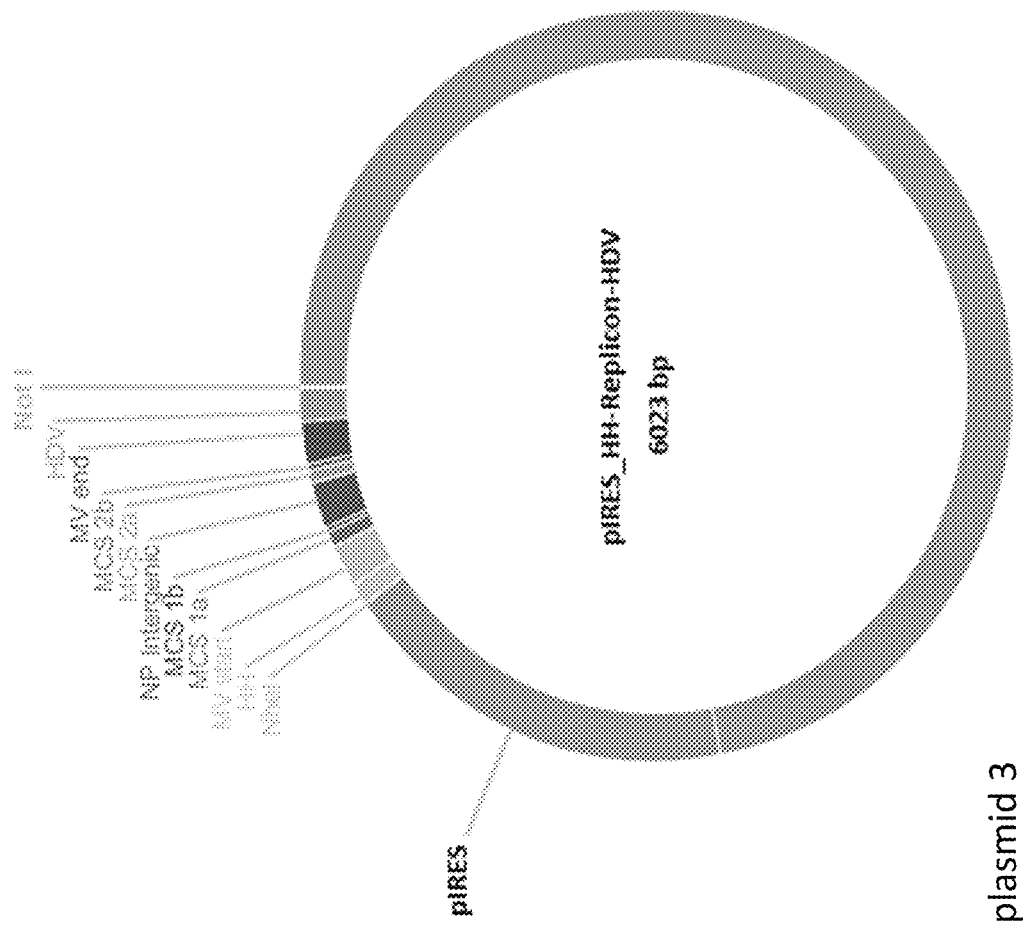
Fig 2C cloning plasmid 3

TWO PLASMID MAMMALIAN EXPRESSION SYSTEM

This application is the U.S. National Phase Application of PCT/IN2012/000405, filed Jun. 8, 2012, which claims priority to Indian Patent Application No. 1679/MUM/2011, filed Jun. 8, 2011, the contents of such applications being incorporated by reference herein.

FIELD OF INVENTION

The present invention relates to a two plasmid mammalian expression system. Moreover invention relates to production of recombinant proteins and viruses. Moreover the present invention relates to a mammalian expression system incorporating methodology for reconstitution of Ribonucleic acid (RNA) dependent RNA polymerase enzyme of negative stranded RNA viruses and its exploitation as a mammalian expression system for the production of proteins, RNA molecules and recombinant viruses.

BACKGROUND OF INVENTION

Advances in molecular biology and genetic engineering led to the development of "Reverse Genetics", a process of generating recombinant viruses from a cloned complimentary DNA (cDNA) copy of a viral genome. It has helped understand the molecular determinants related to virus attenuation, tissue tropism virulence factors and in recent years, accelerated the development of virus vaccines by enabling easy modification of viral genomes through manipulation of its cDNA. Reverse genetics has made it possible to produce recombinant viruses with attenuating mutations or chimeric viruses expressing heterologous genes for use as new viral vaccines or therapeutic agents. Morbilli Viruses (Measles Virus and Rinderpest Virus)

MV and RPV are members of the genus morbillivirus of family Paramyxoviridae. Their genetic information is encoded on a single stranded RNA genome of antisense polarity and comprises 15894(MV) and 15882 (RPV) nucleotides respectively. Their genome has unique highly conserved 3' and 5' termini called leader and trailer respectively and encodes 6 genes—N (nucleocapsid protein), P (phosphoprotein), M (matrix protein), F (fusion protein), H (hemagglutinin) and L (large protein=polymerase)—separated by similarly conserved intergenic sequences. In infected cells, viral RNA dependent RNA polymerase (RDRP) initiates transcription of genomic RNA from its promoter present within the leader sequence and produces messenger ribonucleic acid (mRNA) molecules which are translated into corresponding proteins by the cellular ribosomes. At some point in the viral lifecycle and after adequate pools of viral proteins are synthesized, the RDRP enzyme switches mode and initiates replication from another promoter present within the leader sequence of the genomic RNA. Although the exact mechanism(s) regulating the initiation of transcription or replication of viral RNA and transcription start and stop at gene boundaries is poorly understood, the conserved sequences which serve as promoters for transcription and replication and sequences which dictate the transcription start and end at each gene boundary are clearly defined in case of most negative stranded RNA viruses in general and MV and RPV in particular. It is well established that addition of these sequences to any unrelated RNA molecule forms a "virus genome like replicon" which can be transcribed and replicated by its cognate RDRP.

MV causes an acute febrile illness in infants and young children. Its prevalence can be controlled very effectively by vaccination. Most of the currently used live attenuated vaccines including the Schwartz, Moraten, and Edmonston-Zagreb strains are derived from the original Edmonston strain (Enders and Peebles, 1954) by multiple passages in non human cells (Enders, 1962). However, according to the estimates of the World Health Organisation (WHO), one million young children die every year from measles mainly in developing countries. But in recent years developed countries such as the USA with incomplete adherence to vaccination have seen emergence of measles related deaths (Clements and Cutts, 1995). For a recent discussion of MV vaccinology including future trends see Norrby (1995). During the past 60 odd years, Measles vaccine has been administered in over 700 million children and has proved to be highly effective, usually providing life-long immunity against MV reinfection.

RPV causes cattle plague—an infectious viral disease of cattle, buffalo and other wild life species and is mainly India, Africa and other tropical countries. It is characterized by fever, oral erosions, diarrhea, lymphoid necrosis and high mortality. Two vaccines—Plowright (Plowright and Ferris, 1962) and Lapinized (Scot 1963) have been widely used to protect against rinderpest. The Plowright vaccine derived by attenuation of RBOK strain of RPV has proved to be most effective (Baron et al, 2005). Wide spread use of these vaccines helped irradicate RPV from several countries including India by 2000. However, its reemergence in 2003 has led to resumption of mass vaccinations of cattle and other susceptible animals (Kock et al, 2006).

The proven safety and efficacy of these vaccines, supports their use as an ideal vector for the expression of heterologous genes. Reverse genetics offers a powerful approach for developing recombinant MV or RPV useful as potential vaccines against unrelated diseases and/or therapeutic agents in man and animals.

Reverse genetics was first used to generate RNA viruses by Racaniello and Baltimore in 1981 in case of Poliovirus. Subsequently, several other positive-sense RNA viruses were generated using synthetic RNA produced by T7 or T3 RNA polymerase (Racaniello, V. R. & Baltimore, D., 1981) from a cloned cDNA. Generation of negative stranded RNA viruses however, proved more difficult. Unlike positive stranded RNA viruses, the genome of negative sense viruses cannot be translated by host cells and is not infectious. It must be supplied in the form of ribonucleoprotein (RNP) complexes containing the nucleoprotein and the viral RDRP proteins to allow its transcription and replication and subsequent virus formation. Enami et al, (1990) developed the first reverse genetics system to produce influenza virus (which consists of 9 genomic RNA subunits). Its RNPs are small in size and can be assembled in vitro from RNA and required viral proteins—N and the polymerase components. Initially an artificial RNA carrying a reporter gene—chloramphenicol acetyl transferase (CAT) sequence embedded in viral non-coding terminal sequences of the influenza virus genome subunit was used (Luytjes et al., 1989). Later, single authentic or altered genome subunit RNAs transcribed in vitro from cloned DNA were also used (Enami and Palese, 1991). The assembled RNPs replicated and transcribed upon transfection into influenza-infected cells, as monitored by CAT production and by rescue of a influenza virus, respectively. Purification of virus containing the introduced subunit from the vast excess of non-reassorted virus in some cases can be accomplished by selection, for example, using a specific neutralising antibody directed against the protein encoded by the cognate subunit of the helper virus.

The RNPs of nonsegmented negative-strand RNA viruses (Mononegavirales) contains in addition to N protein, the assembly and polymerase cofactor phosphoprotein (P) and the viral RNA polymerase (large protein L) and are more difficult to assemble in vitro from synthetic RNA and individual proteins. Therefore, many researchers preferred to use smaller subgenomic RNAs (viral minigenomes) containing the essential sequences of viral genome produced during virus lifecycle were used. They were then substituted by artificially transcribed RNA molecules from DNA constructs containing reporter genes and viral essential non-coding sequences (replicons). Replication of such replicons carrying the CAT coding sequence and viral noncoding terminal sequences was achieved for Sendai virus (Park et al., 1991), Sendai. virus (SeV), respiratory syncytial virus (Collins et al., 1993; Collins et al., 1991), human parainfluenza virus 3 (Dimock and Collins, 1993), rabies virus (RV) (Conzelmann and Schnell, 1994) and MV (Sidhu et al., 1995).

A similar system was used to rescue vesicular stomatitis virus (VSV) (Lawson et al., 1995; Schnell, et al, 1994) and rabies virus (RV) entirely from a full length cDNA clone of viral genome under the control T7 RNA polymerase promoter. The components of the viral polymerase complex including the nucleoprotein (NP) were provided from protein expression plasmids that were controlled by T7 RNA polymerase promoter. Soon other researchers also reported generation of non-segmented negative-sense RNA viruses from cloned genomic cDNA for vesicular stomatitis virus (Whelan, et al, 1995), measles virus (Radecke et al, 1995), respiratory syncytial virus (Collins, et al, 1995), sendai virus (Garcin, et al, 1995; Kato et al, 1996), rinderpest virus (Baron & Barrett 1997), human parainfluenza virus (Hoffman et al, 1997; Durbin et al, 1997), simian virus (He et al, 1997), newcastle disease virus (Peeters, et al, 1999) and human severe acute respiratory syndrome corona virus (Yount, et al, 2003).

These demonstrations and other studies of reconstitution of RNA dependent RNA polymerase (RDRP) enzyme activity and its ability to rescue corresponding RNA viruses or non-viral reporter proteins from minireplicons have establish the RDRP enzyme as a powerful versatile system for expression of recombinant proteins either alone or as integral parts of rescued viruses.

The most common methodology used for this purpose, uses transfection of multiple plasmids—one expressing the substrate RNA (a cDNA encoding viral genome or an artificial replicon) and others expressing the viral RDRP complex proteins—viz. the nucleocapsid (N or NP protein), the phosphoprotein (P) and the large polymerase (L) protein and an external T7 RNA polymerase (T7RNAP) to allow expression from these plasmids. The T7 RNAP is used for multiple reasons—(1) its high efficiency, (2) its ability to synthesize RNA with correct 5' terminus identical to viral genome and (3) its ability to transcribe DNA molecules within the cytoplasm thus eliminating modifications of vRNA by RNA splicing, polyadenylation or other mechanisms.

T7RNAP is not a mammalian enzyme. Therefore Pattnaik et al, (1990) used a recombinant attenuated vaccinia virus (VV) (e.g. MVA/T7). It was used for recovery of VSV (Lawson et al, 1995) and rabies virus (Conzelman, U.S. Pat. No. 6,033,886), RSV (Collins et al, 1995); the SV5 (He et al, 1997), HPIV-3 (Durbin et al, 1997), rinderpest virus (Barn and Barrett 1997) and measles virus (Schneider et al, 1997), mumps virus (Clarke et al, 2000), CDV (Gassen et al, 2000), HPIV-2 (Kawano et al, 2001) and BPIV-3 (Schmidt et al, 2000). Similarly, a recombinant fowlpox virus expressing T7RNAP has also been used to supply T7RNAP for recovery of newcastle virus (NDV) (Peeters et at. 1999) and of a chimeric rinderpest virus (Das et al. 2000).

The recombinant viruses produced using this approach are mixed with vaccinia virus and are difficult to purify which can be a major problem—especially if the recombinant viruses are required for preparing immunogenic compositions or gene therapy vectors. Moreover, this helper vaccinia virus kills the host cells limiting the efficiency of recombinant virus production. Therefore, it would be desirable to eliminate the use of helper virus supplying T7 RNA polymerase. Three different approaches have been used to eliminate the use of externally supplied T7RNAP altogether.

Radecke et al, (1995) produced a helper cell line constitutively expressing T7RNAP and Measles virus (MV) N and P proteins (WO 97/06270) and introduction of a plasmid encoding the entire (+) strand sequence of MV genome linked to T7RNAP promoter and another plasmid encoding MV L protein alone is sufficient to rescue recombinant MV. However, the efficiency of this helper cell line is usually limited and requires to be enhanced by giving a heat shock (Parks et al, 1999). Also, this cell line is only useful for rescue of MV. In contrast, the helper BHK-21 cell line (BSR 17/5) stably expresses only the T7RNAP and can be used for rescue of different viruses as shown in case of BRSV (Buchholz et al. 2000), rabies virus (Finke and Conzelmann 1999), VSV (Harty et al. 2001), NDV (Romer-Oberdorfer et al. 1999), and Ebola virus (Volchkov et al. 2001). It can be used to reconstitute RDRP of any virus by co-transfecting with plasmids encoding appropriate N, P and L proteins.

Second approach involves the use of RNA polymerase I (RNAPI). RNAPI is usually involved in transcription of ribosomal genes in mammalian cells. The RNAs synthesized by RNAPI do not contain the 5' methyl cap structure and 3' poly-A tail. The transcription initiation and termination signals for RNAPI are precisely defined and RNA molecules produced by inserting viral genomic or genome like cDNA molecules in between rRNA promoter and terminator signals possess authentic viral 5' and 3' ends, does not require further processing and can be used as a substrate directly by viral RDRP if expressed. (Zobel et al, 1993, Nucleic acids research, 21:3607-3612; Flick and Petterson, 2001, J. Virol. 75: 1643-1655;). Therefore, RNAPI transcription has been used to synthesize viral genomic or genomic like cDNA from plasmids and used for rescue of viruses in case of Influenza virus (Neumann et al, 1999), Borna disease virus and MV (Martin et al, 2006,1 Viral. 80:5708-5715).

More recently, Martin et al, (2006) have used a third strategy to express viral genomic RNA from transcripts produced by RNA polymerase II (RNAP II). They placed a hammerhead ribozyme immediately upstream of and a genomic hepatitis delta virus ribozyme immediately downstream of the virus genomic sequence. These ribozymes cleaved a genomic RNA with authentic 3' and 5' ends from the RNA transcribed by RNAP II.

Such strategies eliminate the need for helper virus but still require separate helper plasmids expressing the viral N, P and L proteins. Transfection of so many plasmids simultaneously in a cell and ensuring useful levels of expression of the desired proteins for efficient reconstitution of RDRP can be difficult. Availability of a single helper plasmid expressing all desired genes will help increase the efficiency of virus rescue by ensuring that all transfected cells will receive the entire complement of helper proteins necessary for reconstitution of RDRP enzyme activity.

This requirement for multiple plasmids has also restricted the use of RDRP based systems to virus rescue, where as studies with artificial replicons encoding reporter proteins has shown that RDRP mediated expression systems can allow high levels expression of recombinant proteins. Availability of a single helper plasmid/reagent to supply the required N, P and L proteins will help expand the scope of using RDRP enzyme for large scale expression of recombinant proteins. Therefore, there exists a need in the art for new simpler methods and reagents which will allow efficient reconstitution of RDRP activity and its exploitation for expression of recombinant proteins, RNA molecules and/or rescue of recombinant viruses.

Here, we describe the preparation and use of simple easily manipulatable plasmid vector systems which can be used for reconstitution of RDRP enzyme activity and its rescue for expression of recombinant proteins, RNA molecules and rescue of recombinant viruses. For this purpose, we have used the RDRP system of 2 viruses—Measles virus (MV) and Rinderpest virus (RPV) as models. These plasmids can be easily modified to express either non-viral proteins, RNA molecules or the entire viral genomes. This vector system will be useful in development of applications related to protein expression and/or generation of recombinant modified viruses (virus rescue) expressing additional proteins and/or RNA molecules useful for vaccination or other therapeutic purposes.

4. OBJECT OF THE INVENTION

The main object of the present invention is to provide two plasmid mammalian expression system for production of recombinant proteins and viruses Another object is to provide a method for reconstitution of RNA dependent RNA polymerase and its exploitation as a mammalian expression system.

A further object of the inventions is to provide a mammalian expression system for the expression of recombinant proteins, nucleic acid, viruses, RNA molecules.

Still further object of the invention is to provide a mammalian expression system for the intracellular expression of RNA molecules like aptamers, antisense RNA, miRNA, siRNA, ribozymes etc Yet another object of the invention is to provide reagents for production of recombinant viruses useful as vaccines or therapeutic agents.

Another object of the invention is to describe the process of the preparation of such a mammalian expression system.

5. SUMMARY

The present invention features the use of RNA dependent RNA polymerase enzyme of morbilliviruses for expression of proteins, RNA molecules and production of recombinant viruses in mammalian cells. In one aspect this provides a plasmid DNA molecules which express the N, P and L proteins of MV. In another aspect of this invention, it provides another plasmid which expresses easily manipulatable RNA substrate of RDRP which can be used for production of any protein, RNA or modified virus. These plasmids may be used as a reagent kit for expression of proteins or RNA molecules or production of recombinant viruses or combination thereof. Further this invention provides a method for using these plasmids for intracellular expression of RNA molecules which may be useful for modulation of cellular gene expression. These plasmids may be used in the form of cloning kits.

The following terms/abbreviations used in the specification have meanings attributed to them as mentioned hereinbelow.

MV: Measles Virus, RPV: Rinder Pest Virus, RNA: Ribonucleic acid, DNA: Deoxyribonucleic acid, RDRP: RNA Dependent RNA Polymerase, cDNA: Complimentary DNA, -VRNA: Negative sense Viral RNA, RNP: Ribonucleoprotein, P: Phospho Proteins, L: Large Polymerase Proteins, N: Nucleocapsid, CMV:Cytomegalovirus, IRES: Internal Ribosomal Entry Site, CHO Cell Line: Chinese Hamster Ovary Cell Line, RNA Pol I- RNA Polymerase I, MOI: Multiplicity of Infection, siRNA: selective interfering RNA, miRNA: micro RNA, GFP: green fluorescent protein, HGH: human growth hormone

BRIEF DESCRIPTION OF THE DRAWING

FIG. 1: Schematic diagram of the cloning plasmids encoding the Measles Minireplicon encoding 2 reporter genes.

A. Basic replicon Design

B. Construct 1: HH-replicon-HDV

C. Construct 2: P1P-replicon-P1T

FIG. 2: Schematic representation of the Cloning Plasmids created.

Cloning Plasmid 1: Vector pUC57 was used to clone P1P_Replicon_P1T construct.

Cloning plasmid 2: Vector pIRES was used to prepare pIRES_P1P_Replicon_P1T construct.

Cloning plasmid 3: Vector pIRES was used to prepare pIRES_HH_Replicon_HDV.

FIG. 3: Synthesis of cDNA of entire MV-E genome

FIG. 3*a*: Generation of cDNA encoding the entire antigenome of MV-E: Viral RNA was purified using Genejet RNA purification kit (Fermentas) and reverse transcribed using Superscript II and random hexamer primers. This was used to amplify seven overlapping fragments with Superscript Ill and specific primers and cloned into pCDNA3.1 in which the multiple cloning site was replaced with a Nhe I_Not I_Pac I_Pme I linker.

FIG. 3*b*: Plasmid encoding cDNA of MV-E genome: cDNA encoding entire antigenome of MV-E was synthesized by assembling seven overlapping PCR amplified fragments and cloned in Not I and Pme I sites of pCDNA 3.1(−)

FIG. 4: Schematic representation of the two variants of Helper plasmid created.

Helper Plasmid 1: Vector pBiCMV-1 was used to prepare piCMV_MV-N_MV-P_IRES_MV-L.

Helper plasmid 2: Vector pIRES was used to prepare pIRES_MV-N_p2A_MV-P_MV-L.

FIG. 5: Vero cells were co-transfected with Cloning plasmid encoding eGFP and HGH and HPV1 or HPV 2, incubated for 48 hrs at 37° C. and observed for fluorescence and HGH. A: pUC 18 alone; B: pGFP (positive control); C: pUC_P1P-replicon-P1T alone; D: pUC-P1P-replicon-P1T and Helper HPV; E: pIRES-HH-replicon-HDV alone; F: pIRES-HH-replicon-HDV and HPV. Note: Helper plasmids 1 and 2 both were able to supply the N, P and L proteins. Representative pictures of HPV1 alone are shown as they were similar.

FIG. 6: Rescue of segmented MV: Equal quantities of plasmids pCDNA_MVgenome, Cloning plasmid 1 (pIRES_HH-replicon-HDV) and HPV 1 were cotransfected into Vero cells using Xfect, incubated at 37° C. and observed daily for formation of syncytia. MV-E was harvested from the culture supernatant after syncytia formation covered >80% -90% and titrated using TCID5O. Cells were observed simultaneously for expression of EGFP plasmid.
- A: Vero cells transfected with pUC-P1P-rep-P1T, pCDNA-MVgenome & Helper plasmid variant 1;
- B: Vero cells transfected with pIRES-HH-rep-HDV, pCDNA-MVgenome & Helper plasmid variant 1.

DETAILED DESCRIPTION AND EXAMPLES

The present invention relates to expression system that can be easily used for cellular reconstruction of the RDRP enzyme activity for the expression of recombinant proteins or virus rescue. It comprises of two plasmids-1. helper plasmid which expresses N, P and L proteins of MV virus and 2. a Cloning Plasmid which expresses easily manipulatable viral RNA or viral like RNA molecule (minireplicon). The cloning plasmid contains multiple cloning sites (MCS) for easy insertion of DNA encoding target molecule to be expressed. Here MV and RPV are used as model system.

EXAMPLES

The invention will be further described in the following examples, which do not limit the scope of the invention described in the claims.

1. Cells and Viruses

Vero (African green monkey kidney) cells were grown as monolayers in Dulbecco\'s modified Eagle\'s medium (DMEM) supplemented with 5% fetal calf serum (FCS). MRCS cells were grown as monolayers in DMEM supplemented with 10% FCS. Measles virus (Edmonston) (MV-E) strain was purchased from Serum Institute of India (MVAC, $10^3$ TCID50/vial). To prepare a seed stock, Vero or MRCS cells were seeded in 25 sq. cm flasks at $10^5$ cells/flask and incubated for 36 hrs. Cells were then washed with HBSS and seeded with MV-E at a MOI of 0.1 and supplemented with serum free DMEM. Virus was harvested at 24 hr intervals. Virus collected over 72 hrs was pooled together, quantitated and used as seed stock.

2. Plasmid Constructions 2.1 Cloning Plasmid 2.1.1 Designing the replicon construct The MV leader (ntds 1 to 107), MV trailer (ntds 15786 to 15894) and the intergenic region between the protein coding regions for MV-N and MV-P proteins (ntd. No 1686 to 1806) were selected from the AY 486084.1 sequence from Genbank (Baricevic et al, 2005). Coding regions for the green fluorescence protein (eGFP) and human growth hormone (HGH) to be used as reporter proteins were isolated from U55762.1 and NM-000515.3 respectively. All these sequences were assembled in silico into a MV-E genome like replicon containing 2 gene cassettes. Nucleotide sequences corresponding to recognition sites for Afe I, Age I, Asc I, Mlu I, Nru I, Pci I, Sac II, Xho I, Eco RI, Pac I, Pme I, PmI I, Sbf I and Xba I were arranged into 2 oligonucleotides to synthesize 2 multiple cloning sites (MCS1 and MCS 2) and inserted in the replicon around the EGFP and HGH genes. As a result, the EGFP protein appeared to have been cloned within the MCS1 region at Asc I site and HGH protein within MCS 2 at Pac I site (FIG. 1A). The sequence of the replicon without the reporter genes is given in Seq ID No. 1.

The sequence corresponding to a 5' hammer head ribozyme was reconstructed from Combredet et al, (2003) and attached at the 5' end of the replicon. Similarly, sequence for 3' hepatitis delta virus ribozyme was adopted from Walker et al, (2003) and appended at the 3' end of replicon to generate a HH-replicon-HDV construct (FIG. 1B; Seq ID No. 2)

Sequences encoding the promoter for chinese hamster RNA polymerase I (P1P) was selected from Tower et al, (1989) and a terminator sequence for murine RNA polymerase I terminator (P1T) was selected on basis sequences described by Grummt et al, (1985, 1986). The P1P sequence was added at immediately upstream of the 5' terminus (immediately upstream) and PiT sequence was appended immediately downstream of the 3' terminus of replicon to create P1P-replicon-P1T construct (FIG. 1C; Seq ID No. 3).

2.1.2 Synthesis of Cloning Plasmids Sequences corresponding to the HH-replicon-HDV (between Eco RI & Hind III sites) and P1P-replicon-P1T (between Sac I and Hind III sites) were synthesized using the gene synthesis method of Young and Dong (2004) and cloned into pUC57 to create pUC_HH-replicon-HDV and pUC_P1P-replicon-P1T respectively.

They were then subcloned in between Nhe I and Not I sites of pIRES vector from Clonetech to generate pIRES_HH-replicon-HDV and pIRES_P1P-replicon-P1T plasmids. These plasmids were used for testing the RNA dependent RNA polymerase (RDRP) mediated expression of GFP and HGH proteins in mammalian cells.

After confirming that these plasmids expressed GFP and HGH under the control of RDRP, the genes for EGFP and HGH were removed by sequential digestion and ligation with Asc I and Pac I to create 3 variants of, cloning plasmids—Cloning Plasmid variant 1 (HH-replicon-HDV) and Cloning plasmid variant 2 (P1P-replicon-P1T) and Cloning Plasmid Variant 3 (pUC_P1P-replicon-P1T). The different plasmids created are listed in Table 1.

TABLE 1

Different Minireplicon plasmids created.

| No | Name | Description | Sequence No |
|---|---|---|---|
| 1 | Cloning plasmid 1 (pUC-P1P-Rep-P1T) | Replicon under the control of CHO cellular RNA polymerase I promoter and murine RNA polymerase I terminator in pUC57 without reporter genes | Seq ID No. 6 |
| 2 | pUC-HH-Rep-HDV | Replicon flanked by Hammerhead and Hepatitis Delta virus ribozymes at the 5' and 3' termini and cloned in pUC57 vector without reporter genes | Seq ID No. 7 |
| 3 | Cloning plasmid 2 (pIRES-P1P-Rep-P1T) | Replicon under the control of CHO cellular RNA polymerase I promoter and murine RNA polymerase I terminator subcloned into the Nhe I | Seq ID No. 5 |

TABLE 1-continued Different Minireplicon plasmids created.

| No | Name | Description | Sequence No |
|----|------|-------------|-------------|
| | | and Not I sites of pIRES vector from Clonetech without reporter genes | |
| 4 | Cloning plasmid 3 (pIRES-HH-Rep-HDV) | Replicon flanked by Hammerhead and Hepatitis Delta virus ribozymes at the 5' and 3' termini subcloned into the Nhe I and Not I sites of pIRES vector from Clonetech without reporter genes | Seq ID No. 4 |
| 5 | Cloning Plasmid 1 with reporter genes | Replicon containing reporter genes eGFP and HGH under the control of CHO cellular RNA Polymerase I promoter and murine RNA polymerase I terminator cloned in pUC57 | |
| 6 | Cloning Plasmid 2 with reporter genes | Replicon containing reporter genes eGFP and HGH under the control of CHO cellular RNA Polymerase I promoter and murine RNA polymerase I terminator subcloned into Nhe I and Not I sites of pIRES vector from Clonetech. | Seq No F |
| 7 | Cloning Plasmid 3 with reporter genes | Replicon containing reporter genes eGFP and HGH flanked by Hammerhead and Hepatitis Delta virus ribozymes at the 5' and 3' termini subcloned into the Nhe I and Not I sites of pIRES vector from Clonetech | Seq No. G |

2.1.3 Synthesis of cDNA of entire MV-E genome

Figure 3A:
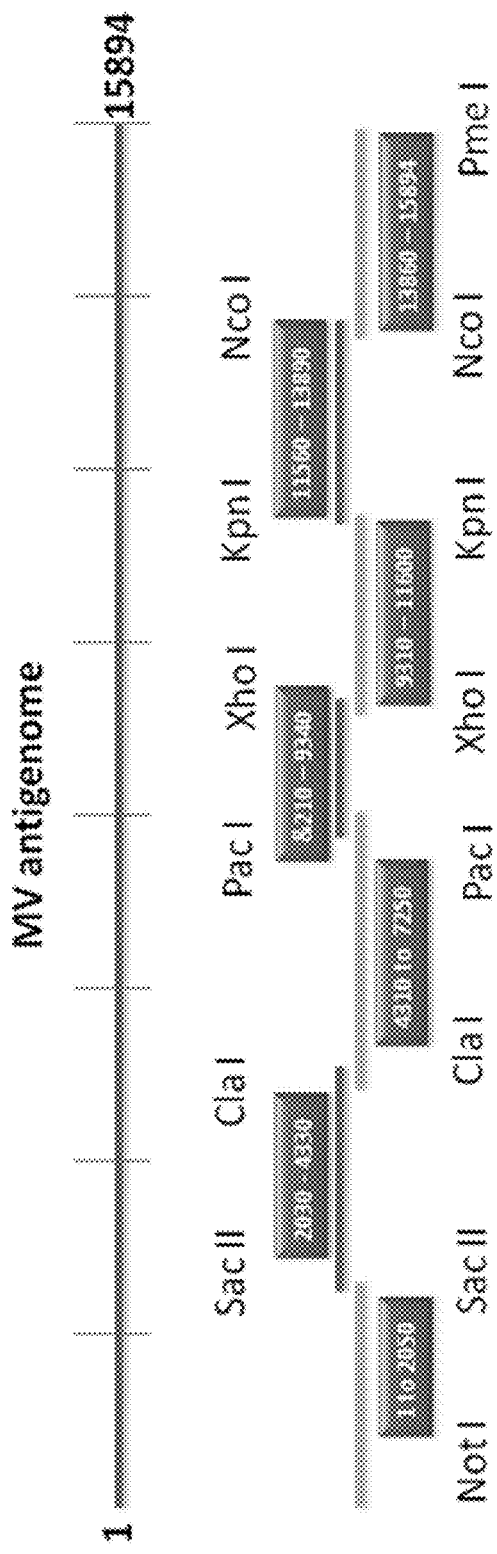

The MV-E cDNA was cloned from viral particles purified from a batch of MV-E vaccinepurchased from the Serum Institute of India, Pune, India. Viral RNA was extracted from 10.sup.5 lysed virus particles using GeneJet RNA purification kit (Fermentas) according to the manufacturer's RNA purification kit according to the manufacturer's protocol. The viral RNA was reverse transcribed into cDNA using random hexamers and Superscript II DNA polymerase. As Seven overlapping cDNA fragments covering the entire viral genome (as shown in FIG. 3a) were generated by PCR using PfuTurbo DNA polymerase and the following primers (1) 5'-GCGGCCGCACCAAAC-3'; (SEQ ID NO: 10)

(2) 5'-CCTGACCGCGGATGC-3'; (SEQ ID NO: 11)

(3) 5'-ACCTCGCATCCGCGG-3'; (SEQ ID NO: 12)

(4) 5'-CCTCCAGAGTAATCGATTAAGG-3'; (SEQ ID NO: 13)

(5) 5'-AATCGATTACTCTGGAGGAGCAG-3'; (SEQ ID NO: 14)

(6) 5'-CTTGCACCCTAAGITTTAATTAACTAC-3'; (SEQ ID NO: 15)

(7) 5'-GAACAATATCGGTAGTTAATTAAAAC-3'; (SEQ ID NO: 16)

(8) 5'-TGAGGGACTCGAGCATACTC-3'; (SEQ ID NO: 17)

(9) 5'-ATAAGATAGTAGCCATCCTGGAGTAT-3'; (SEQ ID NO: 18)

(10) 5'-GTAGGGCCATGTGCTGGG-3'; (SEQ ID NO: 19)

(11) 5'-CATAGCCGTAACAAAAAGGGTAC-3'; (SEQ ID NO: 20)

(12) 5'-GAGCATCAAGTGAAGGACCATG-3'; (SEQ ID NO: 21)

(13) 5'-GCATTGIGGTATTATAGAGCCTATC-3'; (SEQ ID NO: 22)

(14) 5'-CGGTTTAAACCAGACAAAGCTG-3' (SEQ ID NO: 23)

Figure 3B:
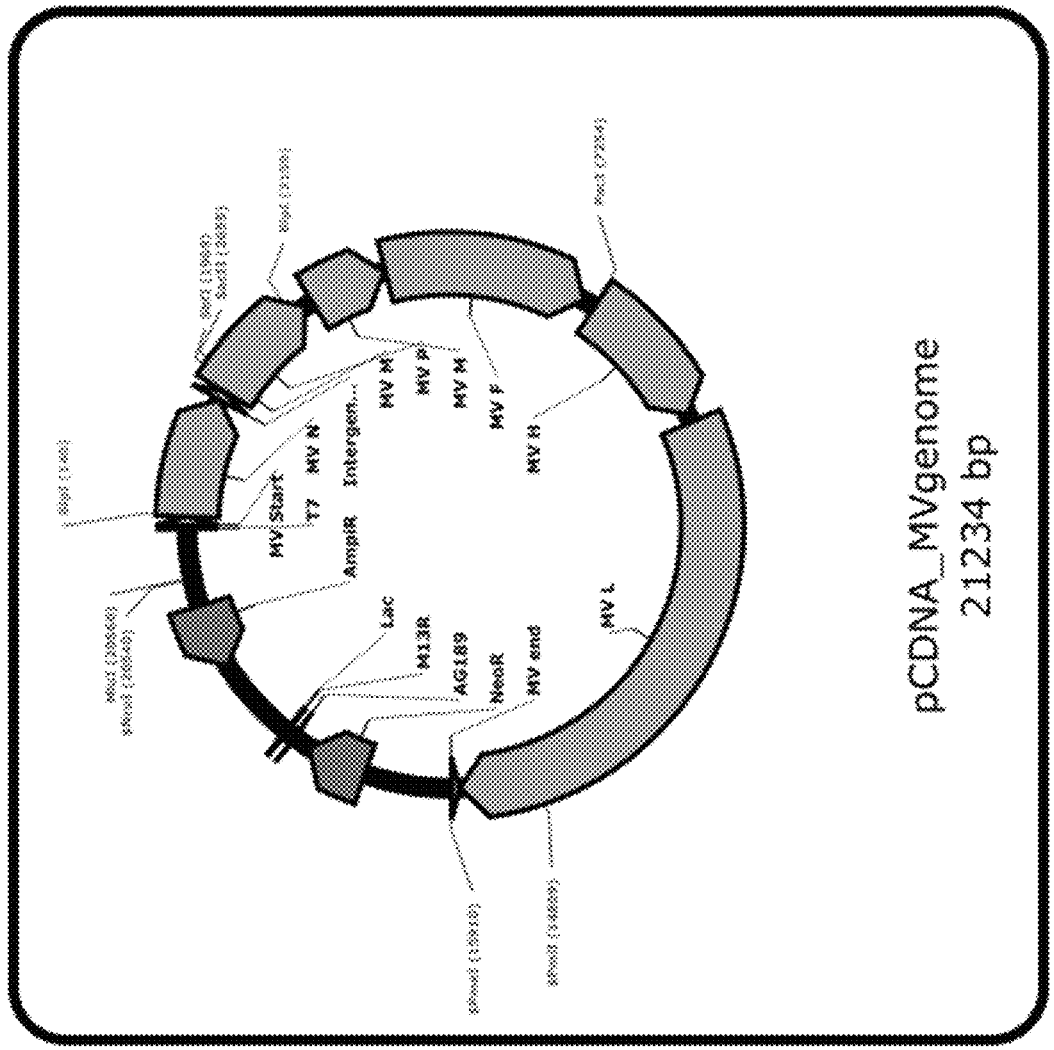

The multiple cloning site from the plasmid pCDNA3.1(-) was removed by digestion with Nhe I and Pme I and replaced it with a linker containing Nhe I-Not I-Pac I-Pme I sites pCDNA-Not_Pac_Pme. The fragments generated by using different primer pairs 7, 8 (Pac I, Xho I), 9,10 (Xho I, Kpn I), 11,12 (Kpn I, Nco I) and 13, 14 (Nco I, Pme I) and ligated into a Pac I-Pme I digested pCDNA-Not_Pac_Pme to generate a plasmid with the nucleotides from Pac I to the 3' end of the MV-E antigenome called pCDNA_Not_Pac MVg_Pme. The fragments generated by other three pairs-1,2 (Not I, Sac II), 3, 4 (Sac II, Cla I), 5, 6(Cla I, Pac I) were ligated into the Not I-Pac I digested pCDNA_Not_PacM-Vg_Pme plasmid to create pCDNA_MVgenome (FIG. 3b).

2.2 Helper Plasmid

RNA was prepared from the purified MV-E virus purchased from Serum Institute of India, Pune, India using the GeneJet RNA purification kit (Fermentas) according to the manufacturer's protocol. 1.mu.g RNA was reverse transcribed using random hexamers and amplified using primers specific for the N (F: 5'-GCTAGCATGGCCACACttt-tAAGG-3' (SEQ ID NO:24) and R 5'-GCGGCCGC-CTAGTCTAGAAGATT-3' (SEQ ID NO:25)), P (F 5'-GCTAGCATGGCAGAAGAGCAGG-3' (SEQ ID NO:26), R 5'-GCGGCCGCCTACTTCATTATTATC-3' (SEQ ID NO:27)) and L (F 5-GCTAGCATGGACTCGC-TATCTGTCAAC-3 (SEQ ID NO:28), R 5-GCGGCCGCT-TAGTCCTTAATCAG -3 (SEQ ID NO:29)) protein coding regions using Superscript III (Invitrogen) as described by Martin et al, (2006) and Combredet et al (2003) using standard molecular cloning techniques. Amplified cDNAs were cloned in between the Nhe I and Not I sites of pIRES vector (Clonetech) to generate pIRES_N, pIRES_P and pIRES_L plasmids.

2.2.1 Synthesis of Helper Plasmid Variant 1

N protein gene was amplified from pIRES_N and subcloned into Eco RI and Pst I sites of pBiCMV1 to generate pBiCMV_N plasmid. The P protein sequence was then amplified and cloned in Nhe I and Eag I sites to create the pBiCMV_NP construct. The L protein sequence was then subcloned in the Eag I and Sal I sites of pBiCMV_ NP plasmid to generate pBiCMV_NPL plasmid. This plasmid contains a bidirectional CMV promoter and can express the N and P proteins. However, the L sequence will be transcribed as a bicistronic RNA with P and will not be translated. Therefore, a mammalian beta globin IRES element (ires) described first, by Chappell et al, (2000) and later on confirmed by Touzlet et al, (2008) to promote efficient translation was inserted immediately upstream of L coding region. An oligonucleotide encoding a pentameric IRES element flanked by a site for Eag I at 5' end and the first 10 nucleotides of L protein at 3' end (5' GGCCGTTCTG ACATCCGGCG GGTTTCTGAC ATCCGGCGGG TTTCTGACAT CCGGCGGGTT TCTGACATCC GGCGGGTTfC TGACATCCGG CGGGTGACTC ACAACGGATC CAACAGACAT ATGGACTCGC 3') (SEQ ID NO:30) was synthesized and inserted by site directed mutagenesis into pBICMV_NPL to generate create pBICMV_NPiresL plasmid which will also be called Helper Plasmid Variant 1(HPV1) (Seq ID No. 8).

2.2.2 Synthesis of Helper Plasmid Variant 2

N protein sequence was amplified and subcloned in between the Nhe I and Xho I sites to obtain pIRES_N. P protein sequence was then amplified from pIRES_P and cloned into the Eco RI and Mlu I sites to create pIRES_NP. Finally, the L sequence was amplified from pIRES_L and cloned into pIRES_NP between the Sal I and Not I sites to obtain pIRES_NPL. In this form, this plasmid will express N and I proteins but not P. Therefore, a strategy based on the recently described 2A peptide vectors was used to promote the expression of P protein (szymczak and Vignali (2005)). The N and P open reading frames from pIRES_NPL were fused by inserting the oligonucleotide (5' ATCTTCTAGA CGGCTCCGGA GCCACGAACT TCTCTCTGTT AAAGCAAGCA GGAGACGTGG AAGAAAACCC CGGTCCCATG GCAGAAGAGC A 3') (SEQ ID NO:31) which encodes the porcine teschovirus 2Apeptide described by Szymczak et at (2007) flanked on the 5' end by the codons immediately before stop codon of MV N protein and on the 3' end by the first few codons of MV P protein by site directed mutagenesis to fuse the N and P protein regions into a single N2AP fusion protein and obtain pIRES_N2aPL plasmid which will also be called Helper Plasmid Variant 2(HPV2) (Seq ID No. 9).

Figure 4A:
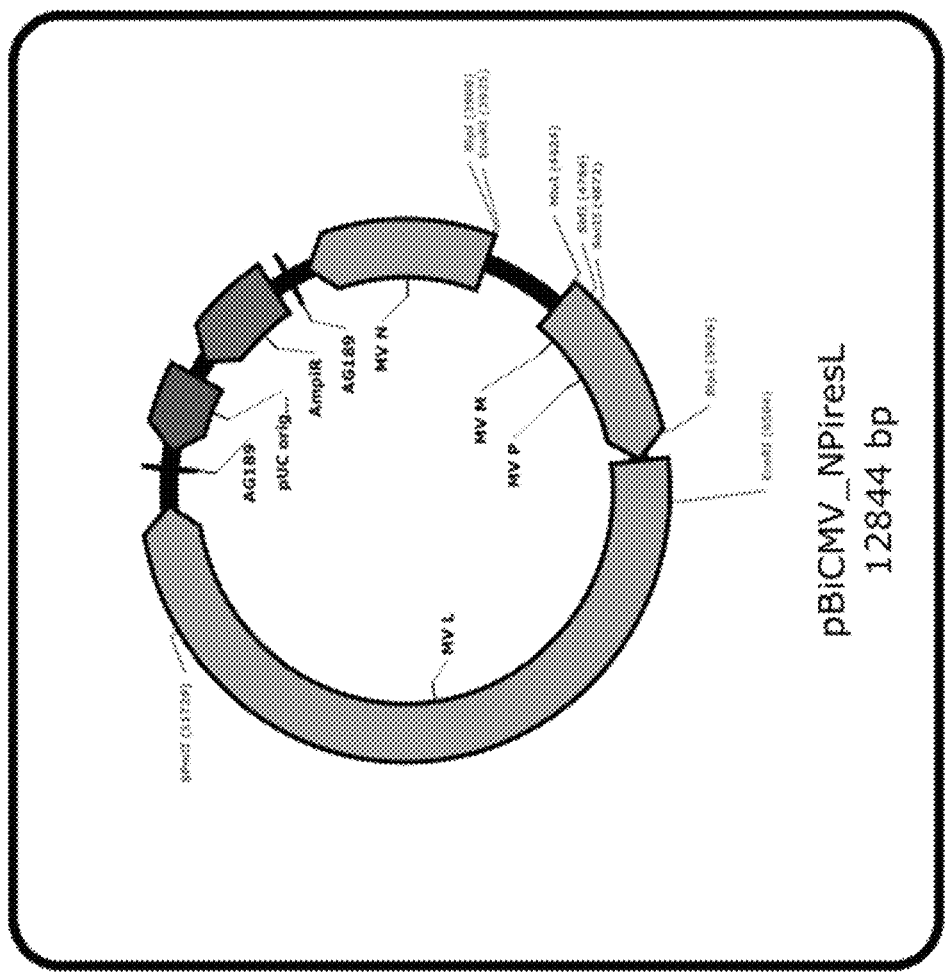
Figure 4B:
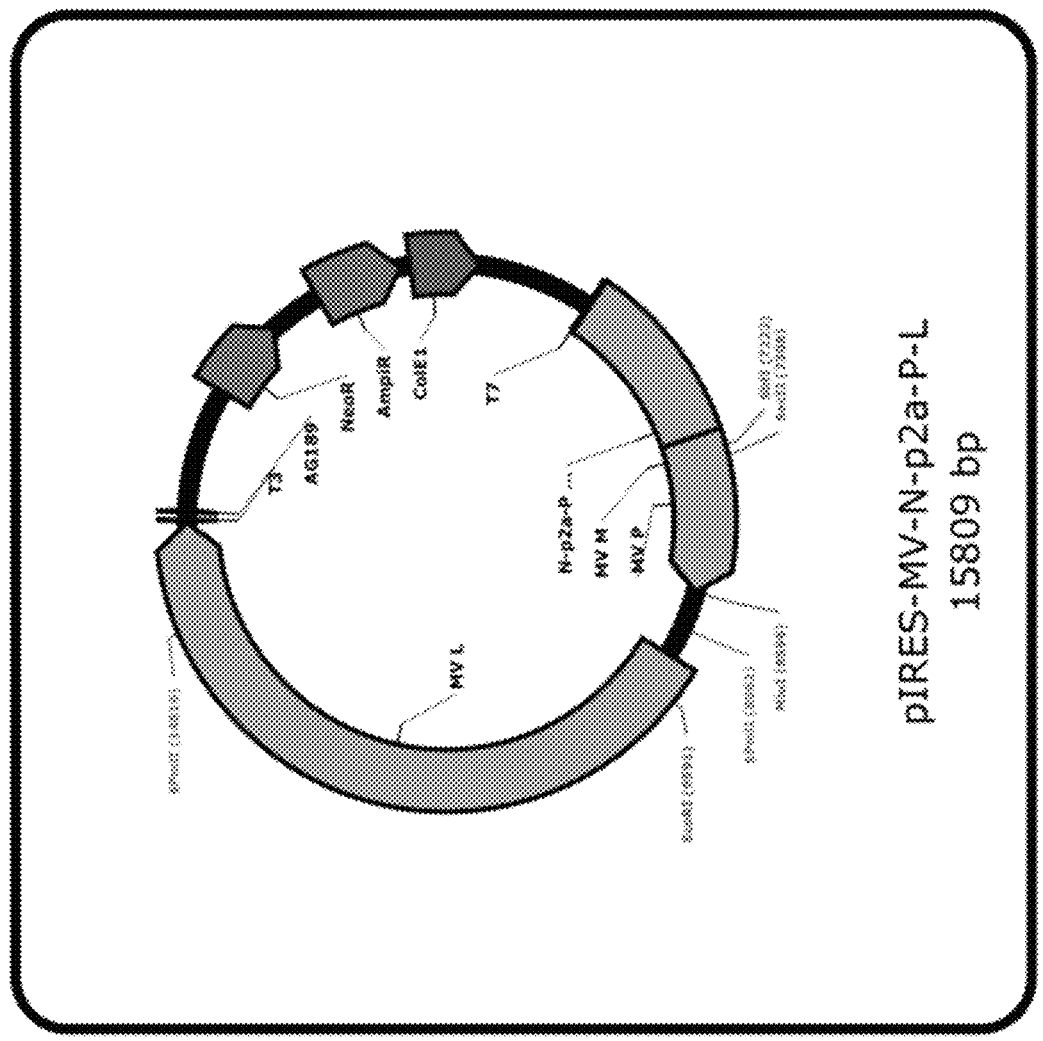
Figure 5A:
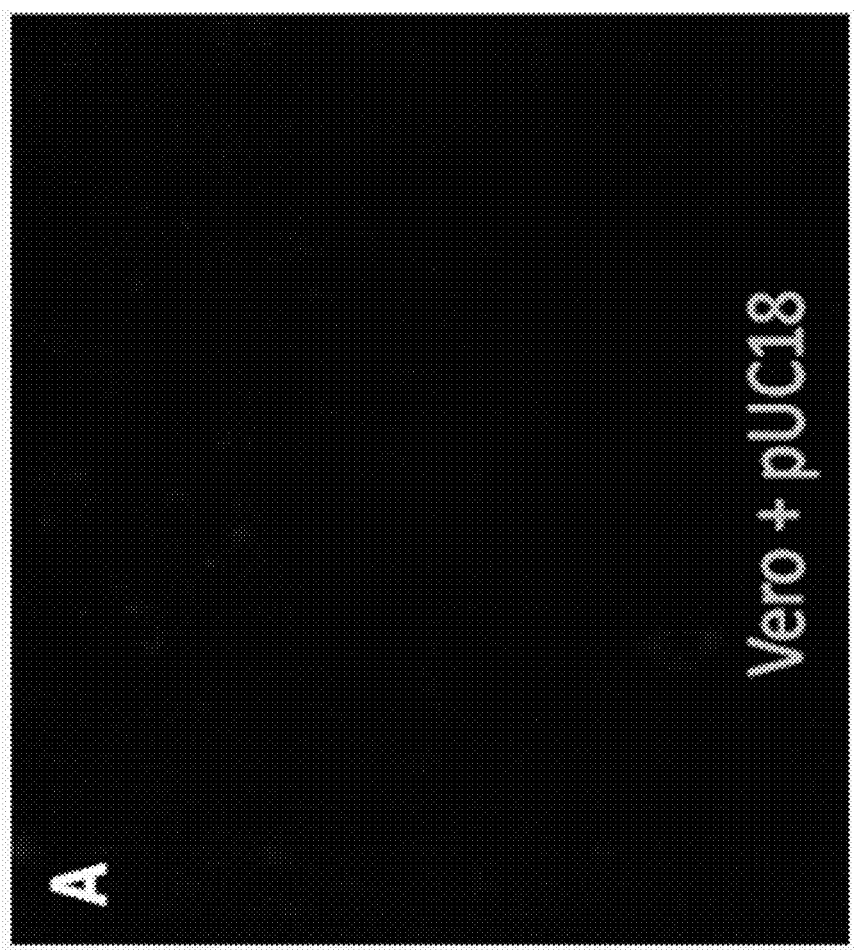
Figure 5B:
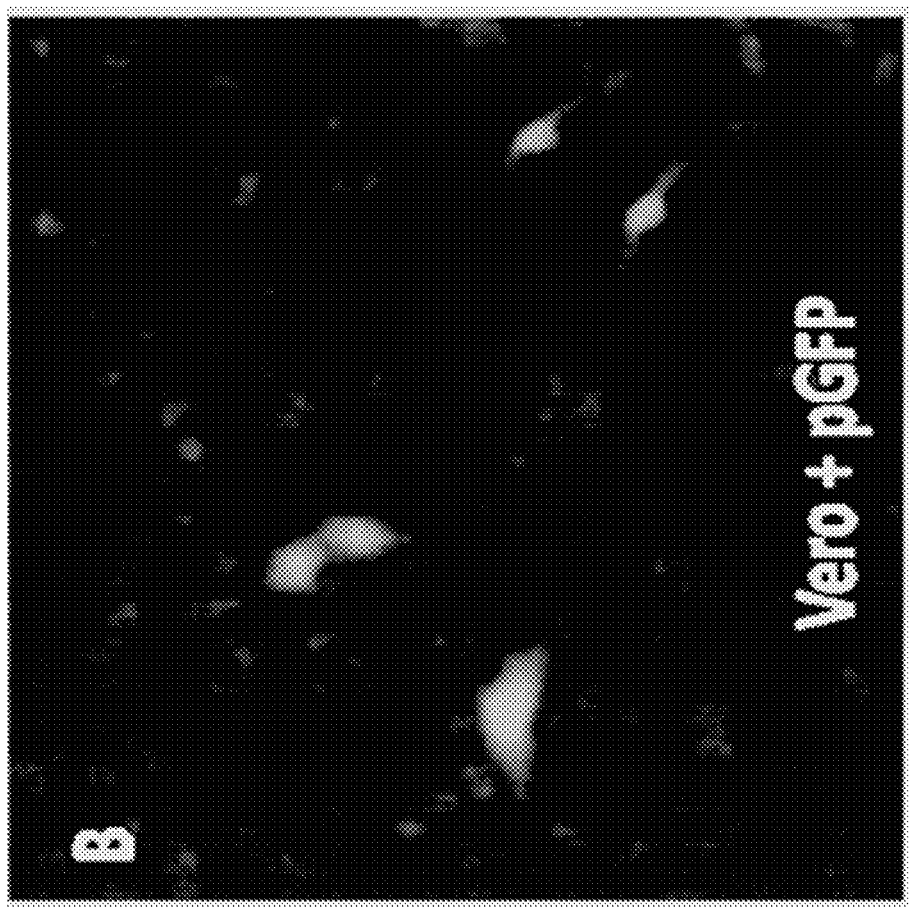
Figure 5C:
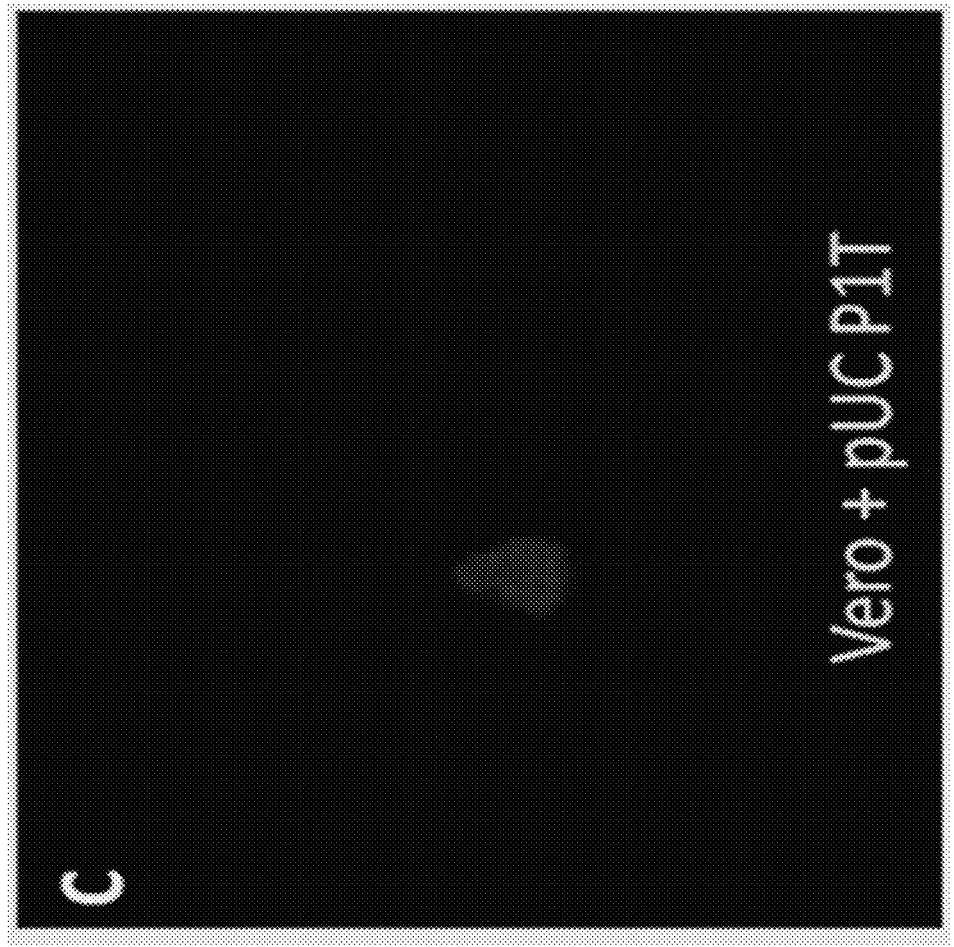
Figure 5D:
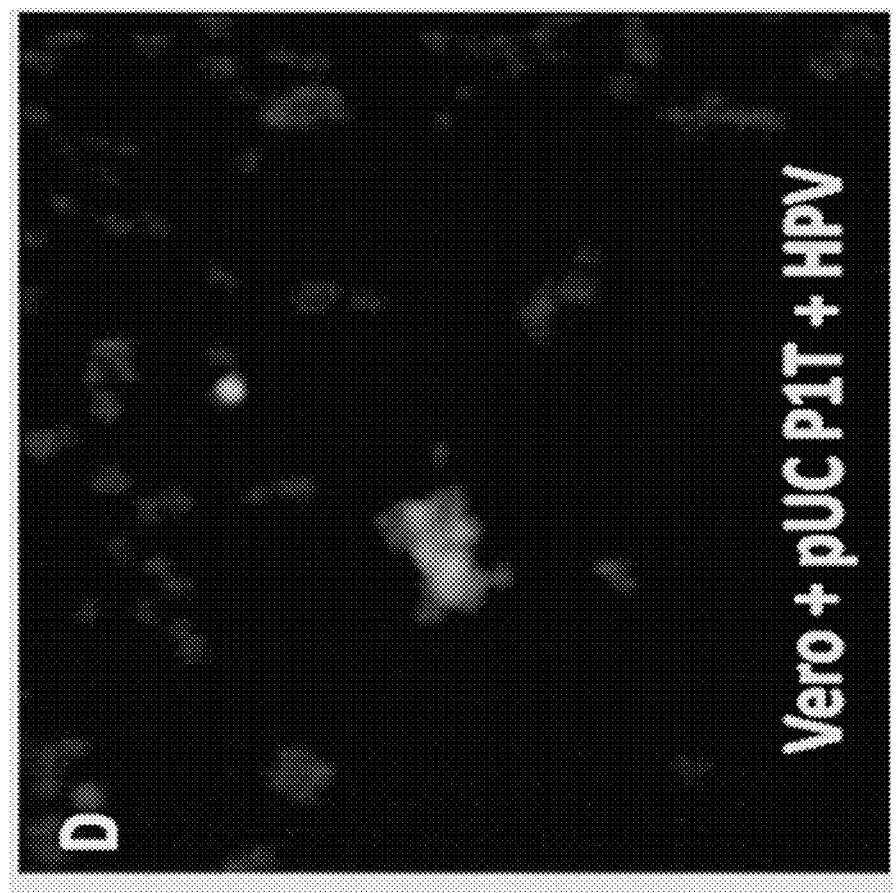
Figure 5E:
Figure 5F:
Figure 6A:
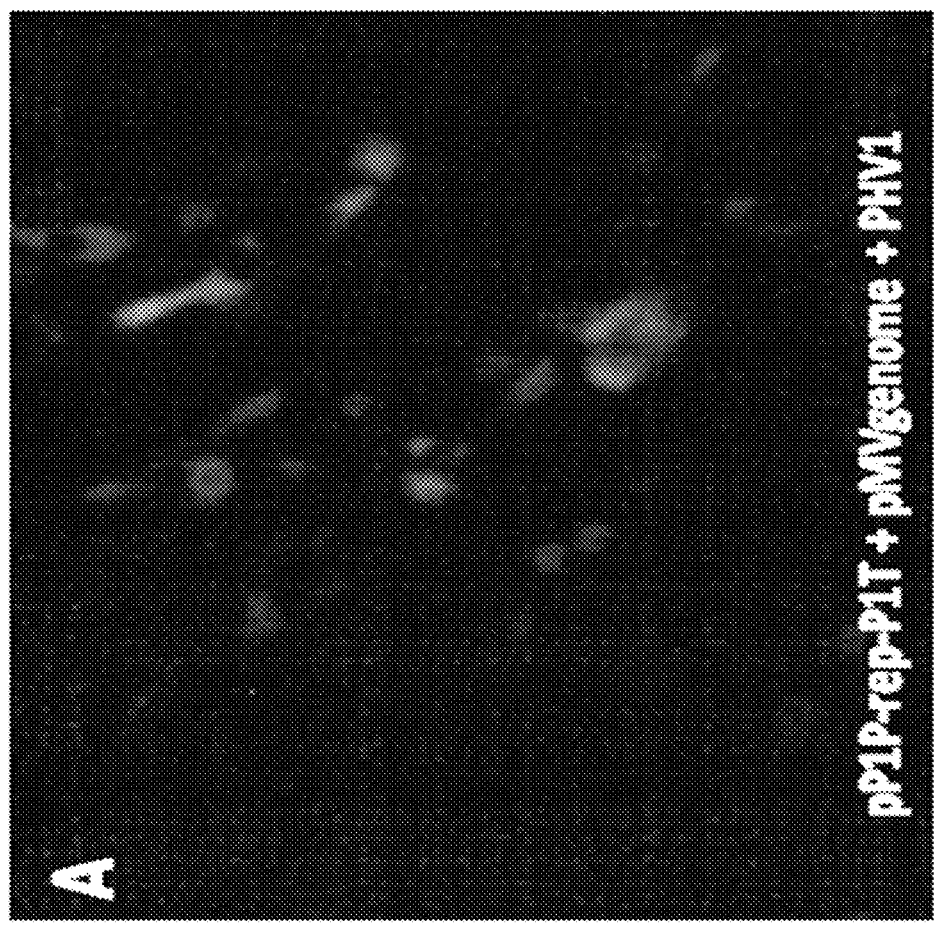
Figure 6B:
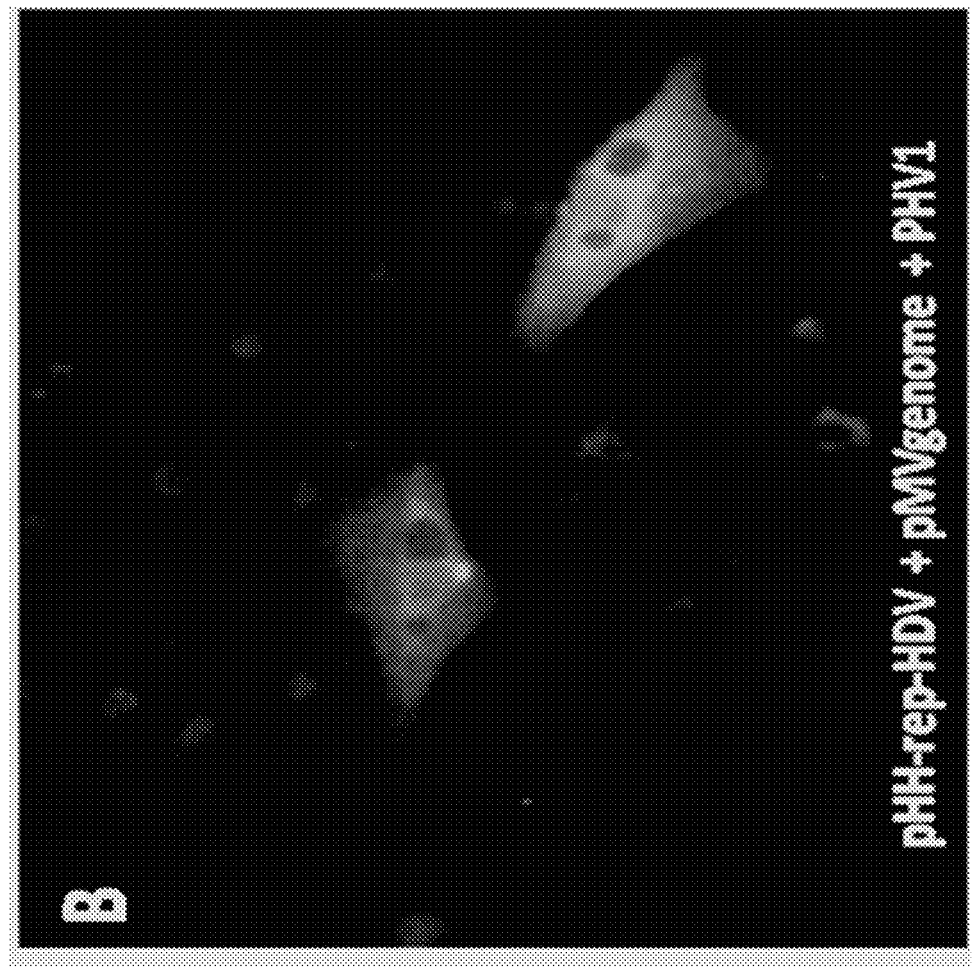

The plasmids HPV1 (pBiCMV_NPiresL) and HPV2 (pIRES_N2aPL) are represented schematically in FIG. 4.

2.2.3 Synthesis of Equivalent Helper Plasmids Encoding N, P and L Proteins of Other Negative Stranded RNA Viruses The cloning strategy used for generation of these helper plasmids was then tested for its applicability to other negative stranded RNA viruses—mainly MV, Rinderpest (RPV); peste des petits ruminants (PPRV) canine distemper (CDV), newcastle disease (NDV) and sendai viruses (SeV). Coding regions of the nucleocapsid, phosphoprotein and large proteins were analysed for the presence of restriction enzymes Eco RI, Pst I, Nhe I, Eag I, Sal I, Xho I, Mlu I and Not I.

Sites for Eco RI and Pst I were absent in the nucleocapsid proteins of MV and CDV. Similarly, sites for Nhe I and Xho I were absent in the nucleocapsid proteins of MV and SeV. However, variable number of sites for enzymes Eco RI, Pst I, Nhe I and Xho I were detected in the nucleocapsid of other viruses (Table 2).

TABLE 2

Presence of sites for Eco RI, Pst I, Nhe I and Xho I in the N protein of various negative stranded RNA viruses

| Virus | Gen bank No | Eco RI | Pst I | Nhe I | Xho I |
|---|---|---|---|---|---|
| MV | AY 486084.1 | 0 | 0 | 0 | 0 |
| RPV | AB 547190.1 | 1 | 3 | 1 | 0 |
| PPRV | HQ197753.1 | 0 | 2 | 0 | 1 |
| CDV | AB 687721.2 | 0 | 1 | 2 | 0 |
| NDV | HQ008337.1 | 0 | 0 | 1 | 2 |
| Sendai | NC_001552.1 | 0 | 1 | 0 | 0 |

Sites for enzymes Eag I, Sal I and Not I were absent from the L proteins of MV, PPRV, CDV and NDV. RPV and SeV contained 1 site for Sal I in their L proteins (Table 3).

TABLE 3

Presence of sites for Eag I, Sal I and Not I in the L proteins of various negative stranded RNA viruses

| Virus | Gen bank No | Eag I | Sal I | Not I |
|---|---|---|---|---|
| MV | AY 486084.1 | 0 | 0 | 0 |
| RPV | AB 547190.1 | 0 | 1 | 1 |
| PPRV | HQ197753.1 | 0 | 0 | 0 |
| CDV | AB 687721.2 | 0 | 0 | 0 |
| NDV | HQ008337.1 | 0 | 0 | 0 |
| Sendai | NC_001552.1 | 0 | 1 | 1 |

However, the genes for both these proteins encode a single protein each. Therefore, it would be easily possible to make synonymous mutations in their protein coding regions and eliminate the sites for these restriction enzymes. Therefore, the same cloning strategy can be easily used to clone the nucleocapsid and Large protein coding regions in a helper plasmid construct similar to either helper plasmid variant 1 or helper plasmid variant 2.

Similar to the above results, analysis of the phosphoprotein coding regions of these viruses revealed the presence of a variable number of sites for enzymes Nhe I, Eag I, Eco RI and Mlu I (Table 4). Sites for these enzymes were absent from the phosphoprotein coding regions of MV, CDV and NDV.

TABLE 3

Presence of sites for Nhe I, Eag I, Eco RI and Mlu I in the P of various negative stranded RNA viruses

| Virus | Gen bank No | Nhe I | Eag I | Eco RI | Mlu I |
|---|---|---|---|---|---|
| MV | AY 486084.1 | 0 | 0 | 0 | 0 |
| RPV | AB 547190.1 | 1 | 0 | 3 | 0 |
| RPV | Z30697.2 | 0 | 0 | 0 | 0 |
| PPRV | HQ197753.1 | 0 | 0 | 1 | 0 |
| CDV | AB 687721.2 | 0 | 0 | 0 | 0 |
| NDV | HQ008337.1 | 0 | 0 | 0 | 0 |
| sendai | NC_001552.1 | 0 | 0 | 1 | 0 |

Although the P protein of RPV (AB547190) sequence is digested by Nhe I and Eco RI the regions corresponding to the recognition sites of these enzymes varies across different strains of RPV (e.g. Z30697.2 in Genbank). On the other hand, the Eco RI site in the P protein of PPRV appears to be highly conserved across most PPRV strains. However, this region of the P protein coding sequence does not overlap with the coding regions of C and V proteins which are also coded by the P gene transcript. Thus, it would be possible to introduce synonymous mutations in the P proteins of RPV and PPRV to enable the use of our proposed strategy for preparing the helper plasmids for MV, CDV, RPV, PPRV and NDV. Therefore, the same restriction enzymes may be used to synthesize helper plasmid constructs equivalent to those described as Helper Plasmid Variant 1 and Helper Plasmid Variant 2 from the nucleocapsid (N or NP), phosphoprotein (P) and large (l) proteins of other negative stranded RNA viruses. Such variants will be useful as helper plasmids for reconstitution of corresponding viral RNA dependent RNA polymerase enzyme and its exploitation for protein or RNA expression and also generation of recombinant viruses as novel vaccines and/or therapeutic agents.

3. Expression of Recombinant Proteins by Plasmid Encoded RDRP

First the capacity of cloning plasmids to express RNA molecules which can serve as substrate for MV RNA dependent RNA polymerase (RDRP) was evaluated using a system similar to the one described by Martin et al, (2006). Briefly, Vero cells were transfected with Cloning plasmid, and individual plasmids expressing the N, P and L proteins of MV-E at a ratio of 1:1:1:0.5 in lipofectamine (Invitrogen) according to the manufacturer's protocol. Cells were incubated at 37° C. in 5% $CO_2$ for 48 hrs and evaluated for expression of green fluorescent protein (eGFP) by microscopy and fluorescence measurement using microplate reader.

In a subsequent experiment, Vero cells were transfected with equal proportions of one cloning plasmid (pUC-P1P-replicon-P1T or pIRES-HH-replicon-HDV or pIRES-P1P-replicon-P1T) and one helper, plasmid (Helper variant 1 or Helper variant 2) in lipofectamine (Invitrogen) or xfect (Clonetech) and incubated at 37° C. in 5% $CO_2$ for 48 hrs and evaluated for the expression of green fluorescent protein (eGFP) by microscopy and fluorescence.

4. Rescue of MV-E

The capacity of the helper plasmids to rescue MV-E from cDNA was tested. Plasmid pCDNA_MVgenome was cotransfected with Helper plasmid variant 1 or Helper plasmid variant 2 in Vero cells using Xfect and incubated overnight at 37° C. Transfection medium was replaced by fresh medium and cells were incubated further for two days. When syncytia involved 80% to 90% of cell layer, virus was harvested by scraping infected cells, freeze-thawing of cells and medium and centrifugation to remove cellular debris. Collected virus was titrated using the TCID50 titration method. Briefly, Vero cells were seeded into 96 well plate (7500 cells/well) and infected by serial 1:10 dilutions of virus sample in DMEM containing 5% DCS. After incubation at 37° C. for 7 days, cells were stained with crystal violet and virus dilution that resulted in infection of 50% of test unit was determined. The 50% end point described as tissue culture infectious dose (TCID50) was calculated by the Kaber method. Virus rescued from the pCDNA_MVgenome+Helper plasmid had titers of $10^6$ to 10' TCID50/ml.

5. Rescue of Segmented MV-E Using Plasmid Encoded RDRP

The capacity of the helper plasmids to rescue recombinant segmented MV-E from cDNA was tested. Vero cells were cotransfected with pCDNA_MVgenome, Cloning plasmid encoding eGFP and either HPV 1 or HPV 2 in equal proportions using Xfect and incubated overnight at 37° C. Transfection medium was replaced by fresh medium and continued to incubate with daily observation for syncytia formation. When syncytia involved 80% to 90% of cell layer, virus was harvested by scraping infected cells, freeze-thawing of cells and medium and centrifugation to remove cellular debris. Collected virus containing was titrated using the TCID50 titration method. Briefly, Vero cells were seeded into 96 well plate (7500 cells/well) and infected by serial 1:10 dilutions of virus sample in DMEM containing 5% DCS. After incubation at 37C for 7 days, cells were stained with crystal violet and virus dilution that resulted in infection of 50% of test unit was determined. The 50% end point described as tissue culture infectious dose (TCID50) was calculated by the Kaber method. Virus rescued from the originally transfected cells had titers of $10^6$ to $10^7$ TCID50/ml. Cells infected with the virus harvested from the originally transfected vero cells also expressed eGFP indicating successful packaging eGFP encoding minireplicon along with MV-E genome into virions and its transfer to fresh cells.

SEQUENCE LISTING

```
<160> NUMBER OF SEQ ID NOS: 31

<210> SEQ ID NO 1
<211> LENGTH: 439
<212> TYPE: DNA
<213> ORGANISM: artificial sequence
<220> FEATURE:
<223> OTHER INFORMATION: Sequence assembled from sequences obtained from
      different organisms or plasmids

<400> SEQUENCE: 1
accaaacaaa gttgggtaag gatagttcaa tcaatgatca ttttctagtg cacttaggat      60
tcaagatcct attatcaggg acaagagcag gattaaggat atccgagtcg cgacgcgtac     120
atgtagcgct cgcaccggtc cgcggggcgc gccctcgagg tgcgagaggc cgaggaccag     180
aacaacatcc gcctaccctc catcattgtt ataaaaaact taggaaccag gtccacacag     240
ccgccagccc atcaaccatc cactcccacg attggagccg cacgtgtcta gagggcccgt     300
ttaaaccctg caggttaatt aagtgaattc ttggttgaac tccggaaccc taatcctgcc     360
ctaggtggtt aggcattatt tgcaatagat taaagaaaac tttgaaaata cgaagtttct     420
attcccagct tgtctggt                                                   439
```

```
<210> SEQ ID NO 2
<211> LENGTH: 614
<212> TYPE: DNA
<213> ORGANISM: artificial sequence
<220> FEATURE:
<223> OTHER INFORMATION: sequence assembled from sequences obtained from
      different organisms or plasmids

<400> SEQUENCE: 2
aagcttgcta gcaccaactt tgtttggtct gatgagtccg tgaggacgaa acccggagtc      60
ccgggtcacc aaacaaagtt gggtaaggat agttcaatca atgatcattt tctagtgcac     120
ttaggattca agatcctatt atcagggaca agagcaggat taaggatatc cgagtcgcga     180
cgcgtacatg tagcgctcgc accggtccgc ggggcgcgcc ggcgcgccct cgaggtgcga     240
gaggccgagg accagaacaa catccgccta ccctccatca ttgttataaa aaacttagga     300
accaggtcca cacagccgcc agcccatcaa ccatccactc ccacgattgg agccgcacgt     360
gtctagaggg cccgtttaaa ccctgcaggt ttaattaagt gaattcttgg ttgaactccg     420
gaaccctaat cctgccctag gtggttaggc attatttgca atagattaaa gaaaactttg     480
aaaatacgaa gtttctattc ccagctttgt ctggtgccgg ccatggtccc agcctcctcg     540
ctggcggccg gtgggcaaca ttccgagggg accgtcccct cggtaatggc gaatgggacc     600
gcggccgcga gctc                                                       614

<210> SEQ ID NO 3
<211> LENGTH: 969
<212> TYPE: DNA
<213> ORGANISM: artificial sequence
<220> FEATURE:
<223> OTHER INFORMATION: sequence assembled from sequences obtained from
      different organisms or plasmids

<400> SEQUENCE: 3
aagcttggct agcacatcct cttggtccta tcacggttat gaggtcgacc agttgttgct      60
ttgatgttcg gttctctcgt tgattgggac aatatttggg gcacttcgcc ggtcccgact     120
tccagaattt ccgtgtggtc tgtgaattta tcaccgctac actgtcatca tattccagtt     180
ttgcaatctg ctctctttgt acctgcagat aggtaccaaa caaagttggg taaggatagt     240
tcaatcaatg atcattttct agtgcactta ggattcaaga tcctattatc agggacaaga     300
gcaggattaa ggatatccga gtcgcgacgc gtacatgtag cgctcgcacc ggtccgcggg     360
gcgcgccctc gaggtgcgag aggccgagga ccagaacaac atccgcctac cctccatcat     420
tgttataaaa aacttaggaa ccaggtccac acagccgcca gcccatcaac catccactcc     480
cacgattgga gccgcacgtg tctagagggc ccgtttaaac cctgcaggtt taattaagtg     540
aattcttggt tgaactccgg aaccctaatc ctgccctagg tggttaggca ttatttgcaa     600
tagattaaag aaaactttga aaatacgaag tttctattcc cagctttgtc tggtttttt      660 ccccccaac ttcggaggtc gaccagtact ccgggcgaca ctttgttttt ttttttttccc     720 ccgatgctgg aggtcgacca gatgtccgaa agtgtccccc ccccccccc ccccccccg      780 gcgcggagcg gcggggccac cccggacccc tttttttttt tttttttttt tttaaattc     840 ctggaacctt taggtcgacc agttgtccgt cttttactcc ttcatatagg tcgaccagta     900
ctccgggtgg tactttgtct ttttctgaaa atcccagagg tcgaccagat atccgcggcc     960
gccgagctc                                                             969
```

<210> SEQ ID NO 4
<211> LENGTH: 6023
<212> TYPE: DNA
<213> ORGANISM: artificial sequence
<220> FEATURE:
<223> OTHER INFORMATION: sequence assembled from sequences obtained from different organisms or plasmids

<400> SEQUENCE: 4

| | | | | | |
|---|---|---|---|---|---|
| ggccgcttcc | ctttagtgag | ggttaatgct | tcgagcagac | atgataagat | acattgatga | 60 |
| gtttggacaa | accacaacta | gaatgcagtg | aaaaaaatgc | tttatttgtg | aaatttgtga | 120 |
| tgctattgct | ttatttgtaa | ccattataag | ctgcaataaa | caagttaaca | acaacaattg | 180 |
| cattcatttt | atgtttcagg | ttcaggggga | gatgtgggag | gttttttaaa | gcaagtaaaa | 240 |
| cctctacaaa | tgtggtaaaa | tccgataagg | atcgatccgg | ctggcgtaa | tagcgaagag | 300 |
| gcccgcaccg | atcgccctcc | ccaacagttg | cgcagcctga | atggcgaatg | gacgcgccct | 360 |
| gtagcggcgc | attaagcgcg | gcgggtgtgg | tggttacgcg | cagcgtgacc | gctacacttg | 420 |
| ccagcgccct | agcgcccgct | cctttcgctt | tcttcccttc | ctttctcgcc | acgttcgccg | 480 |
| gctttccccg | tcaagctcta | aatcgggggc | tccctttagg | gttccgattt | agagctttac | 540 |
| ggcacctcga | ccgcaaaaaa | cttgatttgg | gtgatggttc | acgtagtggg | ccatcgccct | 600 |
| gatagacggt | ttttcgccct | ttgacgttgg | agtccacgtt | ctttaatagt | ggactcttgt | 660 |
| tccaaactgg | aacaacactc | aaccctatct | cggtctattc | ttttgattta | taagggattt | 720 |
| tgccgatttc | ggcctattgg | ttaaaaaatg | agctgattta | acaaatattt | aacgcgaatt | 780 |
| ttaacaaaat | attaacgttt | acaatttcgc | ctgatgcggt | attttctcct | tacgcatctg | 840 |
| tgcggtattt | cacaccgcat | acgcggatct | gcgcagcacc | atggcctgaa | ataacctctg | 900 |
| aaagaggaac | ttggttaggt | accttctgag | gcggaaagaa | ccagctgtgg | aatgtgtgtc | 960 |
| agttagggtg | tggaaagtcc | ccaggctccc | cagcaggcag | aagtatgcaa | agcatgcatc | 1020 |
| tcaattagtc | agcaaccagg | tgtggaaagt | ccccaggctc | cccagcaggc | agaagtatgc | 1080 |
| aaagcatgca | tctcaattag | tcagcaacca | tagtcccgcc | cctaactccg | cccatcccgc | 1140 |
| ccctaactcc | gcccagttcc | gcccattctc | cgccccatgg | ctgactaatt | ttttttattt | 1200 |
| atgcagaggc | cgaggccgcc | tcggcctctg | agctattcca | gaagtagtga | ggaggctttt | 1260 |
| ttggaggcct | aggcttttgc | aaaaagcttg | attcttctga | cacaacagtc | tcgaacttaa | 1320 |
| ggctagagcc | accatgattg | aacaagatgg | attgcacgca | ggttctccgg | ccgcttgggt | 1380 |
| ggagaggcta | ttcggctatg | actgggcaca | acagacaatc | ggctgctctg | atgccgccgt | 1440 |
| gttccggctg | tcagcgcagg | ggcgcccggt | tctttttgtc | aagaccgacc | tgtccggtgc | 1500 |
| cctgaatgaa | ctgcaggacg | aggcagcgcg | gctatcgtgg | ctggccacga | cgggcgttcc | 1560 |
| ttgcgcagct | gtgctcgacg | ttgtcactga | agcgggaagg | gactggctgc | tattgggcga | 1620 |
| agtgccgggg | caggatctcc | tgtcatctca | ccttgctcct | gccgagaaag | tatccatcat | 1680 |
| ggctgatgca | atgcggcggc | tgcatacgct | tgatccggct | acctgcccat | tcgaccacca | 1740 |
| agcgaaacat | cgcatcgagc | gagcacgtac | tcggatggaa | gccggtcttg | tcgatcagga | 1800 |
| tgatctggac | gaagagcatc | aggggctcgc | gccagccgaa | ctgttcgcca | ggctcaaggc | 1860 |
| gcgcatgccc | gacggcgagg | atctcgtcgt | gacccatggc | gatgcctgct | tgccgaatat | 1920 |
| catggtggaa | aatggccgct | tttctggatt | catcgactgt | ggccggctgg | gtgtggcgga | 1980 |
| ccgctatcag | gacatagcgt | tggctacccg | tgatattgct | gaagagcttg | gcggcgaatg | 2040 |

```
ggctgaccgc ttcctcgtgc tttacggtat cgccgctccc gattcgcagc gcatcgcctt    2100
ctatcgcctt cttgacgagt tcttctgagc gggactctgg ggttcgaaat gaccgaccaa    2160
gcgacgccca acctgccatc acgatggccg caataaaata tctttatttt cattacatct    2220
gtgtgttggt ttttttgtgtg aatcgatagc gataaggatc cgcgtatggt gcactctcag    2280
tacaatctgc tctgatgccg catagttaag ccagccccga cacccgccaa cacccgctga    2340
cgcgccctga cgggcttgtc tgctcccggc atccgcttac agacaagctg tgaccgtctc    2400
cgggagctgc atgtgtcaga ggttttcacc gtcatcaccg aaacgcgcga gacgaaaggg    2460
cctcgtgata cgcctatttt tataggttaa tgtcatgata ataatggttt cttagacgtc    2520
aggtggcact tttcggggaa atgtgcgcgg aaccectatt tgtttatttt tctaaataca    2580
ttcaaatatg tatccgctca tgagacaata accctgataa atgcttcaat aatattgaaa    2640
aaggaagagt atgagtattc aacatttccg tgtcgccctt attccctttt ttgcggcatt    2700
ttgccttcct gtttttgctc acccagaaac gctggtgaaa gtaaaagatg ctgaagatca    2760
gttgggtgca cgagtgggtt acatcgaact ggatctcaac agcggtaaga tccttgagag    2820
ttttcgcccc gaagaacgtt ttccaatgat gagcactttt aaagttctgc tatgtggcgc    2880
ggtattatcc cgtattgacg ccgggcaaga gcaactcggt cgccgcatac actattctca    2940
gaatgacttg gttgagtact caccagtcac agaaaagcat cttacggatg gcatgacagt    3000
aagagaatta tgcagtgctg ccataaccat gagtgataac actgcggcca acttacttct    3060
gacaacgatc ggaggaccga aggagctaac cgcttttttg cacaacatgg gggatcatgt    3120
aactcgcctt gatcgttggg aaccggagct gaatgaagcc ataccaaacg acgagcgtga    3180
caccacgatg cctgtagcaa tggcaacaac gttgcgcaaa ctattaactg gcgaactact    3240
tactctagct tcccggcaac aattaataga ctggatggag gcggataaag ttgcaggacc    3300
acttctgcgc tcggcccttc cggctggctg gtttattgct gataaatctg gagccggtga    3360
gcgtgggtct cgcggtatca ttgcagcact ggggccagat ggtaagccct cccgtatcgt    3420
agttatctac acgacgggga gtcaggcaac tatggatgaa cgaaatagac agatcgctga    3480
gataggtgcc tcactgatta gcattggta actgtcagac caagtttact catatatact    3540
ttagattgat ttaaaacttc attttttaatt taaaaggatc taggtgaaga tcctttttga    3600
taatctcatg accaaaatcc cttaacgtga gttttcgttc cactgagcgt cagaccccgt    3660
agaaaagatc aaaggatctt cttgagatcc ttttttttctg cgcgtaatct gctgcttgca    3720
aacaaaaaaa ccaccgctac cagcggtggt ttgtttgccg gatcaagagc taccaactct    3780
ttttccgaag gtaactggct tcagcagagc gcagatacca aatactgtcc ttctagtgta    3840
gccgtagtta ggccaccact tcaagaactc tgtagcaccg cctacatacc tcgctctgct    3900
aatcctgtta ccagtggctg ctgccagtgg cgataagtcg tgtcttaccg ggttggactc    3960
aagacgatag ttaccggata aggcgcagcg gtcgggctga acggggggtt cgtgcacaca    4020
gcccagcttg gagcgaacga cctacaccga actgagatac ctacagcgtg agctatgaga    4080
aagcgccacg cttcccgaag ggagaaaggc ggacaggtat ccggtaagcg cagggtcgg    4140 aacaggagag cgcacgaggg agcttccagg gggaaacgcc tggtatcttt atagtcctgt    4200
cgggtttcgc cacctctgac ttgagcgtcg attttttgtga tgctcgtcag ggggggcggag    4260 cctatggaaa aacgccagca acgcggcctt tttacggttc ctggccttt gctggccttt    4320 tgctcacatg gctcgacaga tcttcaatat tggccattag ccatattatt cattggttat    4380
atagcataaa tcaatattgg ctattggcca ttgcatacgt tgtatctata tcataatatg    4440
```

```
tacatttata ttggctcatg tccaatatga ccgccatgtt ggcattgatt attgactagt    4500
tattaatagt aatcaattac ggggtcatta gttcatagcc catatatgga gttccgcgtt    4560
acataactta cggtaaatgg cccgcctggc tgaccgccca acgaccccg cccattgacg     4620 tcaataatga cgtatgttcc catagtaacg ccaatagga ctttccattg acgtcaatgg     4680
gtggagtatt tacggtaaac tgcccacttg gcagtacatc aagtgtatca tatgccaagt    4740
ccgcccccta ttgacgtcaa tgacggtaaa tggcccgcct ggcattatgc ccagtacatg    4800
accttacggg actttcctac ttggcagtac atctacgtat tagtcatcgc tattaccatg    4860
gtgatgcggt tttggcagta caccaatggg cgtggatagc ggtttgactc acggggattt    4920
ccaagtctcc accccattga cgtcaatggg agtttgtttt ggcaccaaaa tcaacgggac    4980
tttccaaaat gtcgtaacaa ctgcgatcgc ccgcccgtt gacgcaaatg gcggtaggc     5040 gtgtacggtg ggaggtctat ataagcagag ctcgtttagt gaaccgtcag atcactagaa    5100
gctttattgc ggtagtttat cacagttaaa ttgctaacgc agtcagtgct tctgacacaa    5160
cagtctcgaa cttaagctgc agtgactctc ttaaggtagc cttgcagaag ttggtcgtga    5220
ggcactgggc aggtaagtat caaggttaca agacaggttt aaggagacca atagaaactg    5280
ggcttgtcga gacagagaag actcttgcgt ttctgatagg cacctattgg tcttactgac    5340
atccactttg cctttctctc cacaggtgtc cactcccagt tcaattacag ctcttaaggc    5400
tagagtactt aatacgactc actataggct agcaccaact ttgtttggtc tgatgagtcc    5460
gtgaggacga aacccggagt cccgggtcac caaacaaagt tgggtaagga tagttcaatc    5520
aatgatcatt ttctagtgca cttaggattc aagatcctat tatcagggac aagagcagga    5580
ttaaggatat ccgagtcgcg acgcgtacat gtagcgctcg caccggtccg cggggcgcgc    5640
cggcgcgccc tcgaggtgcg agaggccgag gaccagaaca acatccgcct accctccatc    5700
attgttataa aaaacttagg aaccaggtcc acacagccgc cagcccatca accatccact    5760
cccacgattg gagccgcacg tgtctagagg gcccgtttaa accctgcagg tttaattaag    5820
tgaattcttg gttgaactcc ggaacccgaa tcctgccctta ggtggttagg cattatttgc    5880
aatagattaa agaaaacttt gaaaatacga agtttctatt cccagctttg tctggtgccg    5940
gccatggtcc cagcctcctc gctggcggcc ggtgggcaac attccgaggg gaccgtcccc    6000
tcggtaatgg cgaatgggac cgc                                            6023
```

<210> SEQ ID NO 5
<211> LENGTH: 6376
<212> TYPE: DNA
<213> ORGANISM: artificial sequence
<220> FEATURE:
<223> OTHER INFORMATION: sequence assembled from sequences obtained from different organisms or plasmids

<400> SEQUENCE: 5

```
ggccgcttcc ctttagtgag ggttaatgct tcgagcagac atgataagat acattgatga     60
gtttggacaa accacaacta gaatgcagtg aaaaaaatgc tttatttgtg aaatttgtga    120
tgctattgct ttatttgtaa ccattataag ctgcaataaa caagttaaca acaacaattg    180
cattcatttt atgtttcagg ttcagggga gatgtgggag gttttttaaa gcaagtaaaa    240
cctctacaaa tgtggtaaaa tccgataagg atcgatccgg ctggcgtaa tagcgaagag    300 gcccgcaccg atcgccctc caacagttg cgcagcctga atggcgaatg gacgcgccct    360
gtagcggcgc attaagcgcg gcgggtgtgg tggttacgcg cagcgtgacc gctacacttg    420
```

```
ccagcgccct agcgcccgct cctttcgctt tcttcccttc ctttctcgcc acgttcgccg    480
gctttccccg tcaagctcta aatcgggggc tcccttaggg gttccgattt agagctttac    540
ggcacctcga ccgcaaaaaa cttgatttgg gtgatggttc acgtagtggg ccatcgccct    600
gatagacggt ttttcgccct tgacgttgg agtccacgtt ctttaatagt ggactcttgt    660
tccaaactgg aacaacactc aaccctatct cggtctattc ttttgattta aagggatttt    720
tgccgatttc ggcctattgg ttaaaaaatg agctgattta acaaatattt aacgcgaatt    780
ttaacaaaat attaacgttt acaatttcgc ctgatgcggt attttctcct tacgcatctg    840
tgcggtattt cacaccgcat acgcggatct gcgcagcacc atggcctgaa ataacctctg    900
aaagaggaac ttggttaggt accttctgag gcggaaagaa ccagctgtgg aatgtgtgtc    960
agttagggtg tggaaagtcc ccaggctccc cagcaggcag aagtatgcaa agcatgcatc   1020
tcaattagtc agcaaccagg tgtggaaagt ccccaggctc cccagcaggc agaagtatgc   1080
aaagcatgca tctcaattag tcagcaacca tagtcccgcc cctaactccg cccatcccgc   1140
ccctaactcc gcccagttcc gcccattctc cgccccatgg ctgactaatt ttttttattt   1200
atgcagaggc cgaggccgcc tcggcctctg agctattcca gaagtagtga ggaggctttt   1260
ttggaggcct aggcttttgc aaaaagcttg attcttctga cacaacagtc tcgaacttaa   1320
ggctagagcc accatgattg aacaagatgg attgcacgca ggttctccgg ccgcttgggt   1380
ggagaggcta ttcggctatg actgggcaca acagacaatc ggctgctctg atgccgccgt   1440
gttccggctg tcagcgcagg ggcgcccggt tctttttgtc aagaccgacc tgtccggtgc   1500
cctgaatgaa ctgcaggacg aggcagcgcg gctatcgtgg ctggccacga cgggcgttcc   1560
ttgcgcagct gtgctcgacg ttgtcactga agcgggaagg gactggctgc tattgggcga   1620
agtgccgggg caggatctcc tgtcatctca ccttgctcct gccgagaaag tatccatcat   1680
ggctgatgca atgcggcggc tgcatacgct tgatccggct acctgcccat tcgaccacca   1740
agcgaaacat cgcatcgagc gagcacgtac tcggatggaa gccggtcttg tcgatcagga   1800
tgatctggac gaagagcatc aggggctcgc gccagccgaa ctgttcgcca ggctcaaggc   1860
gcgcatgccc gacggcgagg atctcgtcgt gacccatggc gatgcctgct tgccgaatat   1920
catggtggaa aatggccgct tttctggatt catcgactgt ggccggctgg gtgtggcgga   1980
ccgctatcag gacatagcgt tggctacccg tgatattgct gaagagcttg gcggcgaatg   2040
ggctgaccgc ttcctcgtgc tttacggtat cgccgctccc gattcgcagc gcatcgcctt   2100
ctatcgcctt cttgacgagt tcttctgagc gggactctgg ggttcgaaat gaccgaccaa   2160
gcgacgccca acctgccatc acgatggccg caataaaata tctttatttt cattacatct   2220
gtgtgttggt tttttgtgtg aatcgatagc gataaggatc gcgtatggt gcactctcag   2280 tacaatctgc tctgatgccg catagttaag ccagccccga cacccgccaa cacccgctga   2340
cgcgccctga cgggcttgtc tgctcccggc atccgcttac agacaagctg tgaccgtctc   2400
cgggagctgc atgtgtcaga ggttttcacc gtcatcaccg aaacgcgcga cgcgaaaggg   2460
cctcgtgata cgcctatttt tataggttaa tgtcatgata taatggtttt cttagacgtc   2520
aggtggcact tttcggggaa atgtgcgcgg aaccccctatt tgtttatttt tctaaataca   2580
ttcaaatatg tatccgctca tgagacaata accctgataa atgcttcaat aatattgaaa   2640
aaggaagagt atgagtattc aacatttccg tgtcgccctt attcccttt tttgcggcatt   2700 ttgccttcct gtttttgctc acccagaaac gctggtgaaa gtaaaagatg ctgaagatca   2760
```

```
gttgggtgca cgagtgggtt acatcgaact ggatctcaac agcggtaaga tccttgagag    2820
ttttcgcccc gaagaacgtt ttccaatgat gagcactttt aaagttctgc tatgtggcgc    2880
ggtattatcc cgtattgacg ccgggcaaga gcaactcggt cgccgcatac actattctca    2940
gaatgacttg gttgagtact caccagtcac agaaaagcat cttacggatg gcatgacagt    3000
aagagaatta tgcagtgctg ccataaccat gagtgataac actgcggcca acttacttct    3060
gacaacgatc ggaggaccga aggagctaac cgcttttttg cacaacatgg ggatcatgt     3120 aactcgcctt gatcgttggg aaccggagct gaatgaagcc ataccaaacg acgagcgtga    3180
caccacgatg cctgtagcaa tggcaacaac gttgcgcaaa ctattaactg gcgaactact    3240
tactctagct tcccggcaac aattaataga ctggatggag gcggataaag ttgcaggacc    3300
acttctgcgc tcggcccttc cggctggctg gtttattgct gataaatctg gagccggtga    3360
gcgtgggtct cgcggtatca ttgcagcact ggggccagat ggtaagccct cccgtatcgt    3420
agttatctac acgacgggga gtcaggcaac tatggatgaa cgaaatagac agatcgctga    3480
gataggtgcc tcactgatta agcattggta actgtcagac caagtttact catatatact    3540
ttagattgat ttaaaacttc attttaatt taaaaggatc taggtgaaga tcctttttga     3600
taatctcatg accaaaatcc cttaacgtga gttttcgttc cactgagcgt cagacccgt     3660 agaaaagatc aaaggatctt cttgagatcc ttttttttctg cgcgtaatct gctgcttgca   3720
aacaaaaaaa ccaccgctac cagcggtggt ttgtttgccg gatcaagagc taccaactct    3780
ttttccgaag gtaactggct tcagcagagc gcagatacca atactgtcc ttctagtgta     3840 gccgtagtta ggccaccact tcaagaactc tgtagcaccg cctacatacc tcgctctgct    3900
aatcctgtta ccagtggctg ctgccagtgg cgataagtcg tgtcttaccg ggttggactc    3960
aagacgatag ttaccggata aggcgcagcg gtcgggctga acggggggtt cgtgcacaca    4020
gcccagcttg gagcgaacga cctacaccga actgagatac ctacagcgtg agctatgaga    4080
aagcgccacg cttcccgaag ggagaaaggc ggacaggtat ccggtaagcg cagggtcgg     4140 aacaggagag cgcacgaggg agcttccagg gggaaacgcc tggtatcttt atagtcctgt    4200
cgggtttcgc cacctctgac ttgagcgtcg atttttgtga tgctcgtcag gggggcggag    4260
cctatggaaa aacgccagca acgcggcctt tttacggttc ctggccttt gctggccttt     4320 tgctcacatg gctcgacaga tcttcaatat tggccattag ccatattatt cattggttat    4380
atagcataaa tcaatattgg ctattggcca ttgcatacgt tgtatctata tcataatatg    4440
tacatttata ttggctcatg tccaatatga ccgccatgtt ggcattgatt attgactagt    4500
tattaatagt aatcaattac ggggtcatta gttcatagcc catatatgga gttccgcgtt    4560
acataactta cggtaaatgg cccgcctggc tgaccgccca acgacccccg cccattgacg    4620
tcaataatga cgtatgttcc catagtaacg ccaataggga ctttccattg acgtcaatgg    4680
gtggagtatt tacggtaaac tgcccacttg gcagtacatc aagtgtatca tatgccaagt    4740
ccgcccccta ttgacgtcaa tgacggtaaa tggcccgcct ggcattatgc ccagtacatg    4800
accttacggg actttcctac ttggcagtac atctacgtat tagtcatcgc tattaccatg    4860
gtgatgcggt tttggcagta caccaatggg cgtggatagc ggtttgactc acggggattt    4920
ccaagtctcc accccattga cgtcaatggg agtttgtttt ggcaccaaaa tcaacgggac    4980
tttccaaaat gtcgtaacaa ctgcgatcgc ccgccccgtt gacgcaaatg ggcggtaggc    5040
gtgtacggtg ggaggtctat ataagcagag ctcgtttagt gaaccgtcag atcactagaa    5100
gctttattgc ggtagtttat cacagttaaa ttgctaacgc agtcagtgct tctgacacaa    5160
```

```
cagtctcgaa cttaagctgc agtgactctc ttaaggtagc cttgcagaag ttggtcgtga    5220
ggcactgggc aggtaagtat caaggttaca agacaggttt aaggagacca atagaaactg    5280
ggcttgtcga cacagagaag actcttgcgt ttctgatagg cacctattgg tcttactgac    5340
atccactttg cctttctctc cacaggtgtc cactcccagt tcaattacag ctcttaaggc    5400
tagagtactt aatacgactc actataggct agcacatcct cttggtccta tcacggttat    5460
gaggtcgacc agttgttgct ttgatgttcg gttctctcgt tgattgggac aaatatttggg   5520 gcacttcgcc ggtcccgact tccagaattt ccgtgtggtc tgtgaattta tcaccgctac    5580
actgtcatca tattccagtt ttgcaatctg ctctctttgt acctgcagat aggtaccaaa    5640
caaagttggg taaggatagt tcaatcaatg atcatttctc agtgcactta ggattcaaga    5700
tcctattatc agggacaaga gcaggattaa ggatatccga gtcgcgacgc gtacatgtag    5760
cgctcgcacc ggtccgcggg gcgcgccctc gaggtgcgag aggccgagga ccagaacaac    5820
atccgcctac cctccatcat tgttataaaa aacttaggaa ccaggtccac acagccgcca    5880
gcccatcaac catccactcc cacgattgga gccgcacgtg tctagagggc ccgtttaaac    5940
cctgcaggtt taattaagtg aattcttggt tgaactccgg aaccctaatc ctgccctagg    6000
tggttaggca ttatttgcaa tagattaaag aaaactttga aaatacgaag tttctattcc    6060
cagctttgtc tggttttttt cccccccaac ttcggaggtc gaccagtact ccgggcgaca    6120
ctttgttttt tttttttccc ccgatgctgg aggtcgacca gatgtccgaa agtgtccccc    6180
cccccccccc ccccccccg gcgcggagcg gcggggccac cccggacccc ttttttttt     6240 ttttttttt ttttaaattc ctggaacctt taggtcgacc agttgtccgt cttttactcc    6300
ttcatatagg tcgaccagta ctccgggtgg tactttgtct ttttctgaaa atcccagagg    6360
tcgaccagat atccgc                                                    6376
```

<210> SEQ ID NO 6
<211> LENGTH: 3605
<212> TYPE: DNA
<213> ORGANISM: artificial sequence
<220> FEATURE:
<223> OTHER INFORMATION: sequence assembled from sequences obtained from different organisms or plasmids

<400> SEQUENCE: 6

```
agcttggcgt aatcatggtc atagctgttt cctgtgtgaa attgttatcc gctcacaatt     60
ccacacaaca tacgagccgg aagcataaag tgtaaagcct ggggtgccta atgagtgagc    120
taactcacat taattgcgtt gcgctcactg cccgctttcc agtcgggaaa cctgtcgtgc    180
cagctgcatt aatgaatcgg ccaacgcgcg gggagaggcg gtttgcgtat tgggcgctct    240
tccgcttcct cgctcactga ctcgctgcgc tcggtcgttc ggctgcggcg agcggtatca    300
gctcactcaa aggcggtaat acggttatcc acagaatcag gggataacgc aggaaagaac    360
atgtgagcaa aaggccagca aaaggccagg aaccgtaaaa aggccgcgtt gctggcgttt    420
ttccataggc tccgcccccc tgacgagcat cacaaaaatc gacgctcaag tcagaggtgg    480
cgaaacccga caggactata aagataccag gcgtttcccc ctggaagctc cctcgtgcgc    540
tctcctgttc cgaccctgcc gcttaccgga tacctgtccg cctttctccc ttcgggaagc    600
gtggcgcttt ctcatagctc acgctgtagg tatctcagtt cggtgtaggt cgttcgctcc    660
aagctgggct gtgtgcacga accccccgtt cagcccgacc gctgcgcctt atccggtaac    720
tatcgtcttg agtccaaccc ggtaagacac gacttatcgc cactggcagc agccactggt    780
```

```
aacaggatta gcagagcgag gtatgtaggc ggtgctacag agttcttgaa gtggtggcct    840
aactacggct acactagaag aacagtattt ggtatctgcg ctctgctgaa gccagttacc    900
ttcggaaaaa gagttggtag ctcttgatcc ggcaaacaaa ccaccgctgg tagcggtggt    960
ttttttgttt gcaagcagca gattacgcgc agaaaaaaag gatctcaaga agatcctttg   1020 atctttcta cggggtctga cgctcagtgg aacgaaaact cacgttaagg gattttggtc    1080
atgagattat caaaaaggat cttcacctag atccttttaa attaaaaatg aagttttaaa   1140
tcaatctaaa gtatatatga gtaaacttgg tctgacagtt accaatgctt aatcagtgag   1200
gcacctatct cagcgatctg tctatttcgt tcatccatag ttgcctgact ccccgtcgtg   1260
tagataacta cgatacggga gggcttacca tctggcccca gtgctgcaat gataccgcga   1320
gacccacgct caccggctcc agatttatca gcaataaacc agccagccgg aagggccgag   1380
cgcagaagtg gtcctgcaac tttatccgcc tccatccagt ctattaattg ttgccgggaa   1440
gctagagtaa gtagttcgcc agttaatagt ttgcgcaacg ttgttgccat tgctacaggc   1500
atcgtggtgt cacgctcgtc gtttggtatg gcttcattca gctccggttc ccaacgatca   1560
aggcgagtta catgatcccc catgttgtgc aaaaaagcgg ttagctcctt cggtcctccg   1620
atcgttgtca gaagtaagtt ggccgcagtg ttatcactca tggttatggc agcactgcat   1680
aattctctta ctgtcatgcc atccgtaaga tgcttttctg tgactggtga gtactcaacc   1740
aagtcattct gagaatagtg tatgcggcga ccgagttgct cttgcccggc gtcaatacgg   1800
gataataccg cgccacatag cagaacttta aaagtgctca tcattggaaa acgttcttcg   1860 ggcgaaaac tctcaaggat cttaccgctg ttgagatcca gttcgatgta acccactcgt    1920
gcacccaact gatcttcagc atctttttact ttcaccagcg tttctgggtg agcaaaaaca   1980
ggaaggcaaa atgccgcaaa aaagggaata agggcgacac ggaaatgttg aatactcata   2040
ctcttccttt ttcaatatta ttgaagcatt tatcagggtt attgtctcat gagcggatac   2100
atatttgaat gtatttagaa aaataaacaa ataggggttc cgcgcacatt tccccgaaaa   2160
gtgccacctg acgtctaaga aaccattatt atcatgacat taacctataa aaataggcgt   2220
atcacgaggc cctttcgtcc tcgcgcgttt cggtgatgac ggtgaaaacc tctgacacat   2280
gcagctcccg gagacggtca cagcttgtct gtaagcggat gccgggagca gacaagcccg   2340
tcagggcgcg tcagcgggtg ttggcgggtg tcggggctgg cttaactatg cggcatcaga   2400
gcagattgta ctgagagtgc accatatgcg gtgtgaaata ccgcacagat gcgtaaggag   2460
aaaataccgc atcaggcgcc attcgccatt caggctgcgc aactgttggg aagggcgatc   2520
ggtgcgggcc tcttcgctat tacgccagct ggcgaaaggg ggatgtgctg caaggcgatt   2580
aagttgggta acgccaggt tttcccagtc acgacgttgt aaaacgacgg ccagtgaatt   2640
cgagctcggc ggccgcggat atctggtcga cctctgggat tttcagaaaa agacaaagta   2700
ccacccggag tactggtcga cctatatgaa ggagtaaaag acggacaact ggtcgaccta   2760
aaggttccag gaatttaaaa aaaaaaaaa aaaaaaaaa ggggtccggg gtggccccgc     2820
cgctccgcgc cggggggggg gggggggggg ggggacact tcggacatc tggtcgacct     2880 ccagcatcgg gggaaaaaaa aaaacaaag tgtcgcccgg agtactggtc gacctccgaa   2940 gttgggggg aaaaaaacca gacaaagctg ggaatagaaa cttcgtattt tcaaagtttt    3000
ctttaatcta ttgcaaataa tgcctaacca cctagggcag gattagggtt ccggagttca   3060
accaagaatt cacttaatta aacctgcagg gtttaaacgg gccctctaga cacgtgcggc   3120
```

```
tccaatcgtg ggagtggatg gttgatgggc tggcggctgt gtggacctgg ttcctaagtt    3180
ttttataaca atgatggagg gtaggcggat gttgttctgg tcctcggcct ctcgcacctc    3240
gagggcgcgc cccgcggacc ggtgcgagcg ctacatgtac gcgtcgcgac tcggatatcc    3300
ttaatcctgc tcttgtccct gataatagga tcttgaatcc taagtgcact agaaaatgat    3360
cattgattga actatcctta cccaactttg tttggtacct atctgcaggt acaaagagag    3420
cagattgcaa aactggaata tgatgacagt gtagcggtga taaattcaca gaccacacgg    3480
aaattctgga agtcgggacc ggcgaagtgc cccaaatatt gtcccaatca acgagagaac    3540
cgaacatcaa agcaacaact ggtcgacctc ataaccgtga taggaccaag aggatgtgct    3600
agcca                                                                3605
```

<210> SEQ ID NO 7
<211> LENGTH: 3260
<212> TYPE: DNA
<213> ORGANISM: artificial sequence
<220> FEATURE:
<223> OTHER INFORMATION: sequence assembled from sequences obtained from
      different organisms or plasmids

<400> SEQUENCE: 7

```
ctctctcgcg cgtttcggtg atgacggtga aaacctctga cacatgcagc tcccggagac      60
ggtcacagct tgtctgtaag cggatgccgg gagcagacaa gcccgtcagg gcgcgtcagc     120
gggtgttggc gggtgtcggg gctggcttaa ctatgcggca tcagagcaga ttgtactgag     180
agtgcaccat atgcggtgtg aaataccgca cagatgcgta aggagaaaat accgcatcag     240
gcgccattcg ccattcaggc tgcgcaactg ttgggaaggg cgatcggtgc gggcctcttc     300
gctattacgc cagctggcga aggggggatg tgctgcaagg cgattaagtt gggtaacgcc     360
agggttttcc cagtcacgac gttgtaaaac gacggccagt gaattcaagc ttgctagcac     420
caactttgtt tggtctgatg agtccgtgag gacgaaaccc ggagtcccgg gtcaccaaac     480
aaagttgggt aaggatagtt caatcaatga tcatttttcta gtgcacttag gattcaagat     540
cctattatca gggacaagag caggattaag gatatccgag tcgcgacgcg tacatgtagc     600
gctcgcaccg gtccgcgggg cgcgccggcg cgccctcgag gtgcgagagg ccgaggacca     660
gaacaacatc cgcctaccct ccatcattgt tataaaaaac ttaggaacca ggtccacaca     720
gccgccagcc catcaaccat ccactcccac gattggagcc gcacgtgtct agagggcccg     780
tttaaaccct gcaggtttaa ttaagtgaat tcttggttga actccggaac cctaatcctg     840
ccctaggtgt ttaggcatta tttgcaatag attaaagaaa acttttgaaaa tacgaagttt     900 ctattcccag ctttgtctgg tgccggccat ggtcccagcc tcctcgctgg cggccggtgg     960
gcaacattcc gaggggaccg tcccctcggt aatggcgaat gggaccgcgg ccgcgagctc    1020
aagcttggcg taatcatggt catagctgtt tcctgtgtga aattgttatc cgctcacaat    1080
tccacacaac atacgagccg gaagcataaa gtgtaaagcc tggggtgcct aatgagtgag    1140
ctaactcaca ttaattgcgt tgcgctcact gcccgctttc cagtcgggaa acctgtcgtg    1200
ccagctgcat taatgaatcg gccaacgcgc ggggagaggc ggtttgcgta ttgggcgctc    1260
ttccgcttcc tcgctcactg actcgctgcg ctcggtcgtt cggctgcggc gagcggtatc    1320
agctcactca aaggcggtaa tacggttatc cacagaatca ggggataacg caggaaagaa    1380
catgtgagca aaaggccagc aaaaggccag gaaccgtaaa aaggccgcgt tgctggcgtt    1440
tttccatagg ctccgccccc ctgacgagca tcacaaaaat cgacgctcaa gtcagaggtg    1500
```

```
gcgaaacccg acaggactat aaagatacca ggcgtttccc cctggaagct ccctcgtgcg   1560
ctctcctgtt ccgaccctgc cgcttaccgg atacctgtcc gcctttctcc cttcgggaag   1620
cgtggcgctt tctcatagct cacgctgtag gtatctcagt tcggtgtagg tcgttcgctc   1680
caagctgggc tgtgtgcacg aacccccgt tcagcccgac cgctgcgcct tatccggtaa   1740
ctatcgtctt gagtccaacc cggtaagaca cgacttatcg ccactggcag cagccactgg   1800
taacaggatt agcagagcga ggtatgtagg cggtgctaca gagttcttga agtggtggcc   1860
taactacggc tacactagaa gaacagtatt tggtatctgc gctctgctga agccagttac   1920
cttcggaaaa agagttggta gctcttgatc cggcaaacaa accaccgctg gtagcggtgg   1980
tttttttgtt tgcaagcagc agattacgcg cagaaaaaaa ggatctcaag aagatccttt   2040
gatcttttct acgggtctg acgctcagtg gaacgaaaac tcacgttaag ggattttggt   2100
catgagatta tcaaaaagga tcttcaccta gatcctttta aattaaaaat gaagttttaa   2160
atcaatctaa agtatatatg agtaaacttg gtctgacagt taccaatgct taatcagtga   2220
ggcacctatc tcagcgatct gtctatttcg ttcatccata gttgcctgac tccccgtcgt   2280
gtagataact acgatacggg agggcttacc atctggcccc agtgctgcaa tgataccgcg   2340
agacccacgc tcaccggctc cagatttatc agcaataaac cagccagccg aagggccga   2400 gcgcagaagt ggtcctgcaa ctttatccgc ctccatccag tctattaatt gttgccggga   2460
agctagagta agtagttcgc cagttaatag tttgcgcaac gttgttgcca ttgctacagg   2520
catcgtggtg tcacgctcgt cgtttggtat ggcttcattc agctccggtt cccaacgatc   2580
aaggcgagtt acatgatccc ccatgttgtg caaaaaagcg gttagctcct tcggtcctcc   2640
gatcgttgtc agaagtaagt tggccgcagt gttatcactc atggttatgg cagcactgca   2700
taattctctt actgtcatgc catccgtaag atgcttttct gtgactggtg agtactcaac   2760
caagtcattc tgagaatagt gtatgcggcg accgagttgc tcttgcccgg cgtcaatacg   2820
ggataatacc gcgccacata gcagaacttt aaaagtgctc atcattggaa aacgttcttc   2880
ggggcgaaaa ctctcaagga tcttaccgct gttgagatcc agttcgatgt aacccactcg   2940
tgcacccaac tgatcttcag catctttttac tttcaccagc gtttctgggt gagcaaaaac   3000
aggaaggcaa aatgccgcaa aaaagggaat aagggcgaca cggaaatgtt gaatactcat   3060
actcttcctt tttcaatatt attgaagcat ttatcagggt tattgtctca tgagcggata   3120
catatttgaa tgtatttaga aaaataaaca ataggggtt ccgcgcacat tccccgaaa   3180 agtgccacct gacgtctaag aaaccattat tatcatgaca ttaacctata aaaataggcg   3240
tatcacgagg cccttttcgtc                                             3260
```

<210> SEQ ID NO 8
<211> LENGTH: 12844
<212> TYPE: DNA
<213> ORGANISM: artificial sequence
<220> FEATURE:
<223> OTHER INFORMATION: sequence assembled from sequences obtained from
      different organisms or plasmids

<400> SEQUENCE: 8

```
tcgacgatat ctccagagga tcataatcag ccataccaca tttgtagagg ttttacttgc     60
tttaaaaaac ctcccacacc tccccctgaa cctgaaacat aaaatgaatg caattgttgt    120
tgttaacttg tttattgcag cttataatgg ttacaaataa agcaatagca tcacaaattt    180
cacaaataaa gcattttttt cactgccccg agcttcctcg ctcactgact cgctgcgctc    240
```

-continued

```
ggtcgttcgg ctgcggcgag cggtatcagc tcactcaaag gcggtaatac ggttatccac    300
agaatcaggg gataacgcag gaaagaacat gtgagcaaaa ggccagcaaa aggccaggaa    360
ccgtaaaaag gccgcgttgc tggcgttttt ccataggctc cgcccccctg acgagcatca    420
caaaaatcga cgctcaagtc agaggtggcg aaacccgaca ggactataaa gataccaggc    480
gtttccccct ggaagctccc tcgtgcgctc tcctgttccg accctgccgc ttaccggata    540
cctgtccgcc tttctccctt cgggaagcgt ggcgctttct caatgctcac gctgtaggta    600
tctcagttcg gtgtaggtcg ttcgctccaa gctgggctgt gtgcacgaac cccccgttca    660
gcccgaccgc tgcgccttat ccggtaacta tcgtcttgag tccaacccgg taagacacga    720
cttatcgcca ctggcagcag ccactggtaa caggattagc agagcgaggt atgtaggcgg    780
tgctacagag ttcttgaagt ggtggcctaa ctacggctac actagaagga cagtatttgg    840
tatctgcgct ctgctgaagc cagttacctt cggaaaaaga gttggtagct cttgatccgg    900
caaacaaacc accgctggta gcggtggttt ttttgtttgc aagcagcaga ttacgcgcag    960
aaaaaaagga tctcaagaag atcctttgat cttttctacg gggtctgacg ctcagtggaa   1020
cgaaaactca cgttaaggga ttttggtcat gagattatca aaaaggatct tcacctagat   1080
ccttttaaat taaaaatgaa gttttaaatc aatctaaagt atatatgagt aaacttggtc   1140
tgacagttac caatgcttaa tcagtgaggc acctatctca gcgatctgtc tatttcgttc   1200
atccatagtt gcctgactcc ccgtcgtgta gataactacg atacgggagg cttaccatc    1260
tggccccagt gctgcaatga taccgcgaga cccacgctca ccggctccag atttatcagc   1320
aataaaccag ccagccggaa gggccgagcg cagaagtggt cctgcaactt tatccgcctc   1380
catccagtct attaattgtt gccgggaagc tagagtaagt agttcgccag ttaatagttt   1440
gcgcaacgtt gttgccattg ctacaggcat cgtggtgtca cgctcgtcgt ttggtatggc   1500
ttcattcagc tccggttccc aacgatcaag gcgagttaca tgatccccca tgttgtgcaa   1560
aaaagcggtt agctccttcg gtcctccgat cgttgtcaga agtaagttgg ccgcagtgtt   1620
atcactcatg gttatggcag cactgcataa ttctcttact gtcatgccat ccgtaagatg   1680
cttttctgtg actggtgagt actcaaccaa gtcattctga atagtgta tgcggcgacc     1740
gagttgctct tgcccggcgt caatacggga taataccgcg ccacatagca gaactttaaa   1800
agtgctcatc attggaaaac gttcttcggg gcgaaaactc tcaaggatct taccgctgtt   1860
gagatccagt tcgatgtaac ccactcgtgc acccaactga tcttcagcat cttttacttt   1920
caccagcgtt tctgggtgag caaaaacagg aaggcaaaat gccgcaaaaa agggaataag   1980
ggcgacacgg aaatgttgaa tactcatact cttccttttt caatattatt gaagcattta   2040
tcagggttat tgtctcatga gcggatacat atttgaatgt atttagaaaa ataaacaaat   2100
aggggttccg cgcacatttc cccgaaaagt gccacctgac gtcggcagtg aaaaaaatgc   2160
tttatttgtg aaatttgtga tgctattgct ttatttgtaa ccattataag ctgcaataaa   2220
caagttaaca acaacaattg cattcatttt atgtttcagg ttcaggggga ggtgtgggag   2280
gttttttaaa gcaagtaaaa cctctacaaa tgtggtatgg ctgattatga tcctctagac   2340
tgcagactag tttcgaacta gtctagaaga tttctgtcat tgtacactat agggtgtcc    2400
gtgtctgagc cttgttcttc cgagattcct gccatggctt gcagcctaag cagggcgtca   2460
gctgaccttc gactgtcctg cggatcttgg ctggactccg atgcagtgtc aatgtctagg   2520
ggtgtgccgt ttggaagatg ggcagctctc gcatcacttg ctctgctggg cccggtttct   2580
ctgtagctct ccctggcttc tcctcgactc tgtttgaccc tcctatcttc cttgccccc    2640
```

```
aatctcggta gctcattctc actttgatca ccgtgtagaa atgatacttg ggcttgtctg    2700
ggtccaaccg ctctactgat cttgtcctca gtagtatgca ttgcaatctc tgaaacaagc    2760
cttgcatcct cggcagtgat accgagttca gatgccaatg tggaactgac ctttccagct    2820
gacctcctta ccatctcttg ccctaatcta aaatatgctg gatcaaagta agatcggcca    2880
aagttcaaac ctcccatgga gttttcaagt tccactccta ctcccatggc atagctccag    2940
agcagagggt atgatcctgc actgaacttg ttctgaattg agttctccag gattaccatg    3000
tagggtgcag tttcccccat ttgctggtaa aggttcatca aggactcaag tgtggataac    3060
tcaccagcaa attcatgcag tccaagagca ggatacatag tttctatccc aaacttaata    3120
gtcaggataa aactggctaa tcctgcctct acgatatatg tatcaatgtc acatatcatt    3180
tcagcaatcc tgggtttgtt tccgggtgtt ctcttgatat ccaggattag agcgaccatg    3240
aatcggcgta aggagaggtc ctcggcaatc ctgttcctca ccacatccaa ccattttctc    3300
tccaatctaa attcaccaac tacccttctt tgttgggtgt actttatcca ccttcttagc    3360
tccgaatcag ctgccgtgtc tggggccgta accgcctttg cgagcaagac ccaaatttga    3420
gctaggatgg tacccagaat catgttgaat ccctcagggt cttgcacttc aatatctgag    3480
atttccttgt tctcgaacca tccgaacctg gattgatcac tactaattgg atcatcatgt    3540
gaaaagtatt ggtccgcctc atcctccatg ttggtacctc ttgatgcgaa ggtaaggcca    3600
gattgtgact ggtcactctg gacaacctct aacagcctta tgctaacgtc agggtcatcg    3660
gtgatcctct gaatcaattg acctggagac tccacaaata aggataatat acctattagt    3720
gcccctgtta gtttgggccc gctcacatcc gggtttccaa ttaacctgac caaccggtcc    3780
agaagtctgg atcgagtggt aattgaggaa tctccaggga ttggtactat aataatgtgt    3840
ttgattcctc tgatggctcc accggatcct gatgtaatgg gtggtttgtc cttgtttctt    3900
ttgaacaatg ctaagctcct taaaagtgtg gccatgaatt ctccaggcga tctgacggtt    3960
cactaaacga gctctgctta tataggcctc ccaccgtaca cgccacctcg acatactcga    4020
gtagttatta atagtaatca attacggggt cattagttca tagcccatat atggagttcc    4080
gcgttacata acttacggta aatggcccgc ctggctgacc gcccaacgac ccccgcccat    4140
tgacgtcaat aatgacgtat gttcccatag taacgccaat agggactttc cattgacgtc    4200
aatgggtgga gtatttacgg taaactgccc acttggcagt acatcaagtg tatcatatgc    4260
caagtacgcc ccctattgac gtcaatgacg gtaaatggcc cgcctggcat tatgcccagt    4320
acatgacctt atgggacttt cctacttggc agtacatcta cgtattagtc atcgctatta    4380
ccatggtgat gcggttttgg cagtacatca atgggcgtgg atagcggttt gactcacggg    4440
gatttccaag tctccacccc attgacgtca atgggagttt gttttggcac caaaatcaac    4500
gggactttcc aaaatgtcgt aacaactccg ccccattgac gcaaatgggc ggtaggcgtg    4560
tacggtggga ggtctatata agcagagctg gtttagtgaa ccgtcagatc cgctagggat    4620
cctctagtca gctgacgcgt gctagcatgg cagaagagca ggcacgccat gtcaaaaacg    4680
gactggaatg catccgggct ctcaaggccg agcccatcgg ctcactgcc atcgaggaag    4740 ctatggcagc atggtcagaa atatcagaca acccaggaca ggagcgagcc acctgcaggg    4800
aagagaaggc aggcagttcg ggtctcagca accatgcct ctcagcaatt ggatcaactg    4860
aaggcggtgc acctcgcatc cgcggtcagg gacctggaga gagcgatgac gacgctgaaa    4920
ctttgggaat cccccaaga aatctccagg catcaagcac tgggttacag tgttattatg    4980
```

-continued

```
tttatgatca cagcggtgaa gcggttaagg gaatccaaga tgctgactct atcatggttc     5040
aatcaggcct tgatggtgat agcaccctct caggaggaga caatgaatct gaaaacagcg     5100
atgtggatat tggcgaacct gataccgagg gatatgctat cactgaccgg ggatctgctc     5160
ccatctctat ggggttcagg gcttctgatg ttgaaactgc agaaggaggg gagatccacg     5220
agctcctgag actccaatcc agaggcaaca actttccgaa gcttgggaaa actctcaatg     5280
ttcctccgcc tccggacccc ggtagggcca gcacttccgg gacacccatt aaaaagggca     5340
cagacgcgag attagcctca tttggaacgg agatcgcgtc tttattgaca ggtggtgcaa     5400
cccaatgtgc tcgaaagtca ccctcggaac catcagggcc aggtgcacct gcggggaatg     5460
tccccgagtg tgtgagcaat gccgcactga tacaggagtg gacacccgaa tctggtacca     5520
caatctcccc gagatcccag aataatgaag aaggggggaga ctattatgat gatgagctgt     5580
tctctgatgt ccaagatatt aaaacagcct tggccaaaat acgaggat aatcagaaga      5640
taatctccaa gctagaatca ctgctgttat tgaagggaga agttgagtca attaagaagc     5700
agatcaacag gcaaaatatc agcatatcca ccctggaagg acacctctca agcatcatga     5760
tcgccattcc tggacttggg aaggatccca acgaccccac tgcagatgtc gaaatcaatc     5820
ccgacttgaa acccatcata ggcagagatt caggccgagc actggccgaa gttctcaaga     5880
aacccgttgc cagccgacaa ctccaaggaa tgacaaatgg acggaccagt tccagaggac     5940
agctgctgaa ggaatttcag ctaaagccga tcggaaaaaa gatgagctca gccgtcgggt     6000
ttgttcctga caccggccct gcatcacgca gtgtaatccg ctccattata aaatccagcc     6060
ggctagagga ggatcggaag cgttacctga tgactctcct tgatgatatc aaaggagcca     6120
atgatcttgc caagttccac cagatgctga tgaagataat aatgaagtag cggccgttct     6180
gacatccggc gggtttctga catccggcgg gtttctgaca tccggcgggt ttctgacatc     6240
cggcgggttt ctgacatccg gcgggtgact cacaacggat ccaacagaca tatggactcg     6300
ctatctgtca accagatctt ataccctgaa gttcacctag atagcccgat agttaccaat     6360
aagatagtag ccatcctgga gtatgctcga gtccctcacg cttacagcct ggaggaccct     6420
acactgtgtc agaacatcaa gcaccgccta aaaaacggat tttccaacca aatgattata     6480
aacaatgtgg aagttgggaa tgtcatcaag tccaagctta ggagttatcc ggcccactct     6540
catattccat atccaaattg taatcaggat ttatttaaca tagaagacaa agagtcaacg     6600
aggaagatcc gtgaactcct caaaaagggg aattcgctgt actccaaagt cagtgataag     6660
gttttccaat gcttaaggga cactaactca cggcttggcc taggctccga attgagggag     6720
gacatcaagg agaaagttat taacttggga gtttacatgc acagctccca gtggtttgag     6780
cccctttctgt tttggtttac agtcaagact gagatgaggt cagtgattaa atcacaaacc     6840
catacttgcc ataggaggag acacacacct gtattcttca ctggtagttc agttgagttg     6900
ctaatctctc gtgaccttgt tgctataatc agtaaagagt ctcaacatgt atattacctg     6960
acatttgaac tggttttgat gtattgtgat gtcatagagg ggaggttaat gacagagacc     7020
gctatgacta ttgatgctag gtatacagag cttctaggaa gagtcagata catgtggaaa     7080
ctgatagatg gtttcttccc tgcactcggg aatccaactt atcaaattgt agccatgctg     7140
gagcctcttt cacttgctta cctgcagctg agggatataa cagtagaact cagaggtgct     7200
ttccttaacc actgctttac tgaaatacat gatgttcttg accaaaacgg gttttctgat     7260
gaaggtactt atcatgagtt aattgaagct ctagattaca ttttcataac tgatgacata     7320
catctgacag gggagatttt ctcattttc agaagtttcg gccaccccag acttgaagca     7380
```

```
gtaacggctg ctgaaaatgt taggaaatac atgaatcagc ctaaagtcat tgtgtatgag      7440
actctgatga aaggtcatgc catattttgt ggaatcataa tcaacggcta tcgtgacagg      7500
cacggaggca gttggccacc gctgaccctc cccctgcatg ctgcagacac aatccggaat      7560
gctcaagctt caggtgaagg gttaacacat gagcagtgcg ttgataactg gagatctttt      7620
gctggagtga aatttggctg ctttatgcct cttagcctgg atagtgatct gacaatgtac      7680
ctaaaggaca aggcacttgc tgctctccaa agggaatggg attcagttta cccgaaagag      7740
ttcctgcgtt acgaccctcc caagggaacc gggtcacgga ggcttgtaga tgttttcctt      7800
aatgattcga gctttgaccc atatgatgtg ataatgtatg ttgtaagtgg agcttacctc      7860
catgaccctg agttcaacct gtcttacagc ctgaaagaaa aggagatcaa ggaaacaggt      7920
agactttttg ctaaaatgac ttacaaaatg agggcatgcc aagtgattgc tgaaaatcta      7980
atctcaaacg ggattggcaa atattttaag gacaatggga tggccaagga tgagcacgat      8040
ttgactaagg cactccacac tctagctgtc tcaggagtcc ccaaagatct caaagaaagt      8100
cacagggggg ggccagtctt aaaaacctac tcccgaagcc cagtccacac aagtaccagg      8160
aacgtgagag cagcaaaagg gtttataggg ttccctcaag taattcggca ggaccaagac      8220
actgatcatc cggagaatat ggaagcttac gagacagtca gtgcatttat cacgactgat      8280
ctcaagaagt actgccttaa ttggagatat gagaccatca gcttgtttgc acagaggcta      8340
aatgagattt acggattgcc ctcatttttc cagtggctgc ataagaggct tgagacctct      8400
gtcctgtatg taagtgaccc tcattgcccc cccgaccttg acgcccatat cccgttatat      8460
aaagtcccca atgatcaaat cttcattaag tacccctatg gaggtataga agggtattgt      8520
cagaagctgt ggaccatcag caccattccc tatctatacc tggctgctta tgagagcgga      8580
gtaaggattg cttcgttagt gcaaggggac aatcagacca tagccgtaac aaaaagggta      8640
cccagcacat ggccctacaa ccttaagaaa cgggaagctg ctagagtaac tagagattac      8700
tttgtaattc ttaggcaaag gctacatgat attggccatc acctcaaggc aaatgagaca      8760
attgtttcat cacattttttt tgtctattca aaaggaatat attatgatgg gctacttgtg      8820
tcccaatcac tcaagagcat cgcaagatgt gtattctggt cagagactat agttgatgaa      8880
acaagggcag catgcagtaa tattgctaca acaatggcta aaagcatcga gagaggttat      8940
gaccgttacc ttgcatattc cctgaacgtc ctaaaagtga tacagcaaat tctgatctct      9000
cttggcttca caatcaattc aaccatgacc cgggatgtag tcataccccct cctcacgaac      9060 aacgacctct taataaggat ggcactgttg cccgctccta ttgggggggat gaattatctg      9120 aatatgagca ggctgtttgt cagaaacatc ggtgatccag taacatcatc aattgctgat      9180
ctcaagagaa tgattctcgc ctcactaatg cctgaagaga ccctccatca agtaatgaca      9240
caacaaccgg gggactcttc attcctagac tgggctagcg acccttactc agcaaatctt      9300
gtatgtgtcc agagcatcac tagactcctc aagaacataa ctgcaaggtt tgtcctgatc      9360
catagtccaa acccaatgtt aaaaggatta ttccatgatg acagtaaaga agaggacgag      9420
ggactggcgg cattcctcat ggacaggcat attatagtac ctagggcagc tcatgaaatc      9480
ctggatcata gtgtcacagg ggcaagagag tctattgcag gcatgctgga taccacaaaa      9540
ggcctgattc gagccagcat gaggaagggg gggttaacct ctcgagtgat aaccagattg      9600
tccaattatg actatgaaca attcagagca gggatggtgc tattgacagg aagaaagaga      9660
aatgtcctca ttgacaaaga gtcatgttca gtgcagctgg cgagagctct aagaagccat      9720
```

```
atgtgggcga ggctagctcg aggacggcct atttacggcc ttgaggtccc tgatgtacta   9780
gaatctatgc gaggccacct tattcggcgt catgagacat gtgtcatctg cgagtgtgga   9840
tcagtcaact acggatggtt ttttgtcccc tcgggttgcc aactggatga tattgacaag   9900
gaaacatcat ccttgagagt cccatatatt ggttctacca ctgatgagag aacagacatg   9960
aagcttgcct tcgtaagagc cccaagtcga tccttgcgat ctgctgttag aatagcaaca  10020
gtgtactcat gggcttacgg tgatgatgat agctcttgga acgaagcctg gttgttggct  10080
aggcaaaggg ccaatgtgag cctggaggag ctaagggtga tcactcccat ctcaacttcg  10140
actaatttag cgcataggtt gagggatcgt agcactcaag tgaaatactc aggtacatcc  10200
cttgtccgag tggcgaggta taccacaatc tccaacgaca atctctcatt tgtcatatca  10260
gataagaagg ttgatactaa ctttatatac aacaaggaa tgcttctagg gttgggtgtt  10320
ttagaaacat tgtttcgact cgagaaagat accggatcat ctaacacggt attacatctt  10380
cacgtcgaaa cagattgttg cgtgatcccg atgatagatc atcccaggat acccagctcc  10440
cgcaagctag agctgagggc agagctatgt accaacccat tgatatatga taatgcacct  10500
ttaattgaca gagatacaac aaggctatac acccagagcc ataggaggca ccttgtggaa  10560
tttgttacat ggtccacacc ccaactatat cacattttag ctaagtccac agcactatct  10620
atgattgacc tggtaacaaa atttgagaag gaccatatga atgaaatttc agctctcata  10680
ggggatgacg atatcaatag tttcataact gagtttctgc tcatagagcc aagattattc  10740
actatctact tgggccagtg tgcggccatc aattgggcat ttgatgtaca ttatcataga  10800
ccatcaggga aatatcagat gggtgagctg ttgtcatcgt tcctttctag aatgagcaaa  10860
ggagtgttta aggtgcttgt caatgctcta agccacccaa agatctacaa gaaattctgg  10920
cattgtggta ttatagagcc tatccatggt ccttcacttg atgctcaaaa cttgcacaca  10980
actgtgtgca acatggttta cacatgctat atgacctacc tcgacctgtt gttgaatgaa  11040
gagttagaag agttcacatt tctcttgtgt gaaagcgacg aggatgtagt accggacaga  11100
ttcgacaaca tccaggcaaa acacttatgt gttctggcag atttgtactg tcaaccaggg  11160
acctgcccac caattcgagg tctaagaccg gtagagaaat gtgcagttct aaccgaccat  11220
atcaaggcag aggctaggtt atctccagca ggatcttcgt ggaacataaa tccaattatt  11280
gtagaccatt actcatgctc tctgacttat ctccggcgag gatcgatcaa acagataaga  11340
ttgagagttg atccaggatt catttttcgac gccctcgctg aggtaaatgt cagtcagcca  11400
aagatcggca gcaacaacat ctcaaatatg agcatcaagg ctttcagacc cccacacgat  11460
gatgttgcaa aattgctcaa agatatcaac acaagcaagc acaatcttcc catttcaggg  11520
ggcaatctcg ccaattatga aatccatgct ttccgcagaa tcgggttgaa ctcatctgct  11580
tgctacaaag ctgttgagat atcaacatta attaggagat gccttgagcc aggggaggac  11640
ggcttgttct tgggtgaggg atcggggtcc atgttgatca cttataagga gatacttaaa  11700
ctaaacaagt gcttctataa tagtgggggtt tccgccaatt ctagatctgg tcaaagggaa  11760
ttagcaccct atccctccga agttggcctt gtcgaacaca gaatgggagt aggtaatatt  11820
gtcaaagtgc tctttaacgg gaggcccgaa gtcacgtggg taggcagtgt agattgcttc  11880
aatttcatag ttagtaatat ccctacctct agtgtggggt ttatccattc agatatagag  11940
accttgccta acaaagatac tatagagaag ctagaggaat tggcagccat cttatcgatg  12000
gctctgctcc tgggcaaaat aggatcaata ctggtgatta agcttatgcc tttcagcggg  12060
gattttgttc agggatttat aagttatgta gggtcccatt atagagaagt gaaccttgta  12120
```

```
tacccctagat acagcaactt catatctact gaatcttatt tggttatgac agatctcaag    12180
gctaaccggc taatgaatcc tgaaaagatt aagcagcaga taattgaatc atctgtgagg    12240
acttcacctg gacttatagg tcacatccta tccattaagc aactaagctg catacaagca    12300
attgtgggag acgcagttag tagaggtgat atcaatccta ctctgaaaaa acttacacct    12360
atagagcagg tgctgatcaa ttgcgggttg gcaattaacg gacctaagct gtgcaaagaa    12420
ttgatccacc atgatgttgc ctcagggcaa gatggattgc ttaattctat actcatcctc    12480
tacagggagt tggcaagatt caaagacaac caaagaagtc aacaagggat gttccacgct    12540 tacccccgtat tggtaagtag caggcaacga gaacttatat ctaggatcac ccgcaaattt    12600
tgggggcaca ttcttcttta ctccgggaac agaaagttga taaataagtt tatccagaat    12660
ctcaagtccg gctatctgat actagactta caccagaata tcttcgttaa gaatctatcc    12720
aagtcagaga acagattat tatgacgggg ggtttgaaac gtgagtgggt ttttaaggta    12780
acagtcaagg agaccaaaga atggtataag ttagtcggat acagtgccct gattaaggac    12840
taag                                                                 12844
```

<210> SEQ ID NO 9
<211> LENGTH: 15809
<212> TYPE: DNA
<213> ORGANISM: artificial sequence
<220> FEATURE:
<223> OTHER INFORMATION: sequence assembled from sequences obtained from
      different organisms or plasmids

<400> SEQUENCE: 9

```
gcttcccttt agtgagggtt aatgcttcga gcagacatga taagatacat tgatgagttt      60
ggacaaacca caactagaat gcagtgaaaa aaatgcttta tttgtgaaat ttgtgatgct     120
attgctttat ttgtaaccat tataagctgc aataaacaag ttaacaacaa caattgcatt     180
cattttatgt ttcaggttca ggggagatg tgggaggttt tttaaagcaa gtaaaacctc      240
tacaaatgtg gtaaaatccg ataaggatcg atccgggctg gcgtaatagc gaagaggccc     300
gcaccgatcg cccttcccaa cagttgcgca gcctgaatgg cgaatggacg cgccctgtag     360
cggcgcatta agcgcggcgg gtgtggtggt tacgcgcagc gtgaccgcta cacttgccag     420
cgccctagcg cccgctcctt tcgctttctt cccttccttt ctcgccacgt tcgccggctt     480
tccccgtcaa gctctaaatc ggggggctccc tttagggttc cgatttagag ctttacggca     540
cctcgaccgc aaaaaacttg atttgggtga tggttcacgt agtgggccat cgccctgata     600
gacggttttt cgccctttga cgttggagtc cacgttcttt aatagtggac tcttgttcca     660
aactggaaca cactcaacc ctatctcggt ctattctttt gatttataag ggattttgcc     720
gatttcggcc tattggttaa aaaatgagct gatttaacaa atatttaacg cgaattttaa     780
caaaatatta acgtttacaa tttcgcctga tgcggtattt tctccttacg catctgtgcg     840
gtatttcaca ccgcatacgc ggatctgcgc agcaccatgg cctgaaataa cctctgaaag     900
aggaacttgg ttaggtacct tctgaggcgg aaagaaccag ctgtggaatg tgtgtcagtt     960
agggtgtgga aagtccccag gctccccagc aggcagaagt atgcaaagca tgcatctcaa    1020
ttagtcagca accaggtgtg gaaagtcccc aggctcccca gcaggcagaa gtatgcaaag    1080
catgcatctc aattagtcag caaccatagt cccgccccta actccgccca tcccgcccct    1140
aactccgccc agttccgccc attctccgcc ccatggctga ctaatttttt ttatttatgc    1200
agaggccgag gccgcctcgg cctctgagct attccagaag tagtgaggag cttttttggg    1260
```

```
aggcctaggc ttttgcaaaa agcttgattc ttctgacaca acagtctcga acttaaggct    1320
agagccacca tgattgaaca agatggattg cacgcaggtt ctccggccgc ttgggtggag    1380
aggctattcg gctatgactg ggcacaacag acaatcggct gctctgatgc cgccgtgttc    1440
cggctgtcag cgcaggggcg cccggttctt tttgtcaaga ccgacctgtc cggtgccctg    1500
aatgaactgc aggacgaggc agcgcggcta tcgtggctgg ccacgacggg cgttccttgc    1560
gcagctgtgc tcgacgttgt cactgaagcg ggaagggact ggctgctatt gggcgaagtg    1620
ccggggcagg atctcctgtc atctcacctt gctcctgccg agaaagtatc catcatggct    1680
gatgcaatgc ggcggctgca tacgcttgat ccggctacct gcccattcga ccaccaagcg    1740
aaacatcgca tcgagcgagc acgtactcgg atggaagccg gtcttgtcga tcaggatgat    1800
ctggacgaag agcatcaggg gctcgcgcca gccgaactgt tcgccaggct caaggcgcgc    1860
atgcccgacg gcgaggatct cgtcgtgacc catggcgatg cctgcttgcc gaatatcatg    1920
gtggaaaatg gccgcttttc tggattcatc gactgtggcc ggctgggtgt ggcggaccgc    1980
tatcaggaca tagcgttggc tacccgtgat attgctgaag agcttggcgg cgaatgggct    2040
gaccgcttcc tcgtgcttta cggtatcgcc gctcccgatt cgcagcgcat cgccttctat    2100
cgccttcttg acgagttctt ctgagcggga ctctggggtt cgaaatgacc gaccaagcga    2160
cgcccaacct gccatcacga tggccgcaat aaaatatctt tattttcatt acatctgtgt    2220
gttggttttt tgtgtgaatc gatagcgata aggatccgcg tatggtgcac tctcagtaca    2280
atctgctctg atgccgcata gttaagccag ccccgacacc cgccaacacc cgctgacgcg    2340
ccctgacggg cttgtctgct cccggcatcc gcttacagac aagctgtgac cgtctccggg    2400
agctgcatgt gtcagaggtt ttcaccgtca tcaccgaaac gcgcgagacg aaagggcctc    2460
gtgatacgcc tatttttata ggttaatgtc atgataataa tggtttctta cgtcaggt    2520 ggcacttttc ggggaaatgt gcgcggaacc cctatttgtt tatttttcta aatacattca    2580
aatatgtatc cgctcatgag acaataaccc tgataaatgc ttcaataata ttgaaaaagg    2640
aagagtatga gtattcaaca tttccgtgtc gcccttattc ccttttttgc ggcattttgc    2700
cttcctgttt ttgctcaccc agaaacgctg gtgaaagtaa aagatgctga agatcagttg    2760
ggtgcacgag tgggttacat cgaactggat ctcaacagcg gtaagatcct tgagagtttt    2820
cgccccgaag aacgttttcc aatgatgagc acttttaaag ttctgctatg tggcgcggta    2880
ttatcccgta ttgacgccgg gcaagagcaa ctcggtcgcc gcatacacta ttctcagaat    2940
gacttggttg agtactcacc agtcacagaa aagcatctta cggatggcat gacagtaaga    3000
gaattatgca gtgctgccat aaccatgagt gataacactg cggccaactt acttctgaca    3060
acgatcggag gaccgaagga gctaaccgct tttttgcaca acatggggga tcatgtaact    3120
cgccttgatc gttgggaacc ggagctgaat gaagccatac caaacgacga gcgtgacacc    3180
acgatgcctg tagcaatggc aacaacgttg cgcaaactat taactggcga actacttact    3240
ctagcttccc ggcaacaatt aatagactgg atggaggcgg ataaagttgc aggaccactt    3300
ctgcgctcgg cccttccggc tggctggttt attgctgata atctggagcc ggtgagcgt     3360 gggtctcgcg gtatcattgc agcactgggg ccagatggta agccctcccg tatcgtagtt    3420
atctacacga cggggagtca ggcaactatg gatgaacgaa atagacagat cgctgagata    3480
ggtgcctcac tgattaagca ttggtaactg tcagaccaag tttactcata tatactttag    3540
attgatttaa aacttcattt ttaatttaaa aggatctagg tgaagatcct ttttgataat    3600
```

```
ctcatgacca aaatccctta acgtgagttt tcgttccact gagcgtcaga ccccgtagaa    3660
aagatcaaag gatcttcttg agatcctttt tttctgcgcg taatctgctg cttgcaaaca    3720
aaaaaaccac cgctaccagc ggtggttttgt ttgccggatc aagagctacc aactctttttt   3780 ccgaaggtaa ctggcttcag cagagcgcag ataccaaata ctgtccttct agtgtagccg    3840
tagttaggcc accacttcaa gaactctgta gcaccgccta catacctcgc tctgctaatc    3900
ctgttaccag tggctgctgc cagtggcgat aagtcgtgtc ttaccgggtt ggactcaaga    3960
cgatagttac cggataaggc gcagcggtcg ggctgaacgg ggggttcgtg cacacagccc    4020
agcttggagc gaacgaccta caccgaactg agatacctac agcgtgagct atgagaaagc    4080
gccacgcttc ccgaagggag aaaggcggac aggtatccgg taagcggcag ggtcggaaca    4140
ggagagcgca cgagggagct tccaggggga acgcctggt atctttatag tcctgtcggg     4200
tttcgccacc tctgacttga gcgtcgattt ttgtgatgct cgtcaggggg gcggagccta    4260
tggaaaaacg ccagcaacgc ggccttttta cggttcctgg cctttgctg gccttttgct    4320 cacatggctc gacagatctt caatattggc cattagccat attattcatt ggttatatag    4380
cataaatcaa tattggctat tggccattgc atacgttgta tctatatcat aatatgtaca    4440
tttatattgg ctcatgtcca atatgaccgc catgttggca ttgattattg actagttatt    4500
aatagtaatc aattacgggg tcattagttc atagcccata tatggagttc cgcgttacat    4560
aacttacggt aaatggcccg cctggctgac cgcccaacga ccccccgccca ttgacgtcaa    4620 taatgacgta tgttcccata gtaacgccaa tagggacttt ccattgacgt caatgggtgg    4680
agtatttacg gtaaactgcc cacttggcag tacatcaagt gtatcatatg ccaagtccgc    4740
cccctattga cgtcaatgac ggtaaatggc ccgcctggca ttatgcccag tacatgacct    4800
tacgggactt tcctacttgg cagtacatct acgtattagt catcgctatt accatggtga    4860
tgcggttttg gcagtacacc aatgggcgtg atagcggtt tgactcacgg ggatttccaa     4920
gtctccaccc cattgacgtc aatgggagtt tgttttggca ccaaaatcaa cgggactttc    4980
caaaatgtcg taacaactgc gatcgcccgc ccgttgacg caaatgggcg gtaggcgtgt    5040
acggtgggag gtctatataa gcagagctcg tttagtgaac cgtcagatca ctagaagctt    5100
tattgcggta gtttatcaca gttaaattgc taacgcagtc agtgcttctg acacaacagt    5160
ctcgaactta agctgcagtg actctcttaa ggtagcttg cagaagttgg tcgtgaggca    5220
ctgggcaggt aagtatcaag gttacaagac aggtttaagg agaccaatag aaactgggct    5280
tgtcgagaca gagaagactc ttgcgtttct gataggcacc tattggtctt actgacatcc    5340
actttgcctt tctctccaca ggtgtccact cccagttcaa ttacagctct taaggctaga    5400
gtacttaata cgactcacta taggctagca tggccacact tttaaggagc ttagcattgt    5460
tcaaaagaaa caaggacaaa ccacccatta catcaggatc cggtggagcc atcagaggaa    5520
tcaaacacat tattatagta ccaatccctg gagattcctc aattaccact cgatccagac    5580
ttctggaccg gttggtcagg ttaattggaa acccggatgt gagcgggccc aaactaacag    5640
gggcactaat aggtatatta tccttatttg tggagtctcc aggtcaattg attcagagga    5700
tcaccgatga ccctgacgtt agcataaggc tgttagaggt tgtccagagt gaccagtcac    5760
aatctggcct taccttcgca tcaagaggta ccaacatgga ggatgaggcg gaccaatact    5820
tttcacatga tgatccaatt agtagtgatc aatccaggtt cggatggttc gagaacaagg    5880
aaatctcaga tattgaagtg caagaccctg agggattcaa catgattctg ggtaccatcc    5940
tagctcaaat ttgggtcttg ctcgcaaagg cggttacggc cccagacacg gcagctgatt    6000
```

```
cggagctaag aaggtggata aagtacaccc aacaaagaag ggtagttggt gaatttagat    6060
tggagagaaa atggttggat gtggtgagga acaggattgc cgaggacctc tccttacgcc    6120
gattcatggt cgctctaatc ctggatatca agagaacacc cggaaacaaa cccaggattg    6180
ctgaaatgat atgtgacatt gatacatata tcgtagaggc aggattagcc agttttatcc    6240
tgactattaa gtttgggata gaaactatgt atcctgctct tggactgcat gaatttgctg    6300
gtgagttatc cacacttgag tccttgatga acctttacca gcaaatgggg gaaactgcac    6360
cctacatggt aatcctggag aactcaattc agaacaagtt cagtgcagga tcatacccctc   6420 tgctctggag ctatgccatg ggagtaggag tggaacttga aaactccatg ggaggtttga    6480
actttggccg atcttacttt gatccagcat attttagatt agggcaagag atggtaagga    6540
ggtcagctga aaaggtcagt tccacattgg catctgaact cggtatcact gccgaggatg    6600
caaggcttgt ttcagagatt gcaatgcata ctactgagga caagatcagt agagcggttg    6660
gacccagaca agcccaagta tcatttctac acggtgatca aagtgagaat gagctaccga    6720
gattgggggg caaggaagat aggagggtca aacagagtcg aggagaagcc agggagagct    6780
acagagaaac cgggcccagc agagcaagtg atgcgagagc tgcccatctt ccaaccggca    6840 caccccctaga cattgacact gcatcggagt ccagccaaga tccgcaggac agtcgaaggt    6900
cagctgacgc cctgcttagg ctgcaagcca tggcaggaat ctcggaagaa caaggctcag    6960
acacggacac ccctatagtg tacaatgaca gaaatcttct agacggctcc ggagccacga    7020
acttctctct gttaaagcaa gcaggagacg tggaagaaaa ccccggtccc atggcagaag    7080
agcaggcacg ccatgtcaaa aacggactgg aatgcatccg ggctctcaag gccgagccca    7140
tcggctcact ggccatcgag gaagctatgg cagcatggtc agaaatatca gacaacccag    7200
gacaggagcg agccacctgc agggaagaga aggcaggcag ttcgggtctc agcaaaccat    7260
gcctctcagc aattggatca actgaaggcg gtgcacctcg catccgcggt cagggacctg    7320
gagagagcga tgacgacgct gaaactttgg gaatcccccc aagaaatctc caggcatcaa    7380
gcactgggtt acagtgttat tatgtttatg atcacagcgg tgaagcggtt aagggaatcc    7440
aagatgctga ctctatcatg gttcaatcag gccttgatgg tgatagcacc ctctcaggag    7500
gagacaatga atctgaaaac agcgatgtgg atattggcga acctgatacc gagggatatg    7560
ctatcactga ccgggatct gctcccatct ctatggggtt cagggcttct gatgttgaaa    7620
ctgcagaagg aggggagatc cacgagctcc tgagactcca atccagaggc aacaacttc    7680 cgaagcttgg gaaaactctc aatgttcctc cgcctccgga ccccggtagg ccagcactt    7740 ccgggacacc cattaaaaag ggcacagacg cgagattagc ctcatttgga acggagatcg    7800
cgtctttatt gacaggtggt gcaacccaat gtgctcgaaa gtcaccctcg gaaccatcag    7860
ggccaggtgc acctgcgggg aatgtccccg agtgtgtgag caatgccgca ctgatacagg    7920
agtggacacc cgaatctggt accacaatct ccccgagatc ccagaataat gaagaagggg    7980
gagactatta tgatgatgag ctgttctctg atgtccaaga tattaaaaca gccttggcca    8040
aaatacacga ggtaatcag aagataatct ccaagctaga atcactgctg ttattgaagg    8100
gagaagttga gtcaattaag aagcagatca acaggcaaaa tatcagcata tccaccctgg    8160
aaggacacct ctcaagcatc atgatcgcca ttcctggact tgggaaggat cccaacgacc    8220
ccactgcaga tgtcgaaatc aatcccgact gaaacccat cataggcaga gattcaggcc    8280
gagcactggc cgaagttctc aagaaacccg ttgccagccg acaactccaa ggaatgacaa    8340
```

```
atggacggac cagttccaga ggacagctgc tgaaggaatt tcagctaaag ccgatcggga    8400
aaaagatgag ctcagccgtc gggtttgttc ctgacaccgg ccctgcatca cgcagtgtaa    8460
tccgctccat tataaaatcc agccggctag aggaggatcg gaagcgttac ctgatgactc    8520
tccttgatga tatcaaagga gccaatgatc ttgccaagtt ccaccagatg ctgatgaaga    8580
taataatgaa gtagacgcgt cgagcatgca tctagggcgg ccaattccgc ccctctcccc    8640
cccccccctc tccctccccc cccctaacg ttactggccg aagccgcttg gaataaggcc    8700
ggtgtgcgtt tgtctatatg tgattttcca ccatattgcc gtcttttggc aatgtgaggg    8760
cccggaaacc tggccctgtc ttcttgacga gcattcctag gggtcttttcc cctctcgcca    8820 aaggaatgca aggtctgttg aatgtcgtga aggaagcagt tcctctggaa gcttcttgaa    8880
gacaaacaac gtctgtagcg acccctttgca ggcagcggaa cccccaccct ggcgacaggt    8940
gcctctgcgg ccaaaagcca cgtgtataag atacacctgc aaaggcggca caaccccagt    9000
gccacgttgt gagttggata gttgtggaaa gagtcaaatg gctctcctca agcgtattca    9060 acaagggct gaaggatgcc cagaaggtac cccattgtat gggatctgat ctggggcctc    9120
ggtgcacatg ctttacatgt gtttagtcga ggttaaaaaa acgtctaggc ccccgaacc    9180 acggggacgt ggttttcctt tgaaaaacac gatgataagc ttgccacaac ccgggatcct    9240
ctagagtcga catggactcg ctatctgtca accagatctt atacctgaa gttcacctag    9300 atagcccgat agttaccaat aagatagtag ccatcctgga gtatgctcga gtccctcacg    9360
cttacagcct ggaggaccct acactgtgtc agaacatcaa gcaccgccta aaaaacggat    9420
tttccaacca aatgattata acaatgtgg aagttgggaa tgtcatcaag tccaagctta    9480
ggagttatcc ggcccactct catattccat atccaaattg taatcaggat ttatttaaca    9540
tagaagacaa agagtcaacg aggaagatcc gtgaactcct caaaaagggg aattcgctgt    9600
actccaaagt cagtgataag gttttccaat gcttaaggga cactaactca cggcttggcc    9660
taggctccga attgagggag gacatcaagg agaaagttat taacttggga gtttacatgc    9720
acagctccca gtggtttgag ccctttctgt tttggtttac agtcaagact gagatgaggt    9780
cagtgattaa atcacaaacc catacttgcc ataggaggag acacacacct gtattcttca    9840
ctggtagttc agttgagttg ctaatctctc gtgaccttgt tgctataatc agtaaagagt    9900
ctcaacatgt atattacctg acatttgaac tggttttgat gtattgtgat gtcatagagg    9960
ggaggttaat gacagagacc gctatgacta ttgatgctag gtatacagag cttctaggaa    10020
gagtcagata catgtggaaa ctgatagatg gtttcttccc tgcactcggg aatccaactt    10080
atcaaattgt agccatgctg gagcctcttt cacttgctta cctgcagctg agggatataa    10140
cagtagaact cagaggtgct ttccttaacc actgctttac tgaaatacat gatgttcttg    10200
accaaaacgg gttttctgat gaaggtactt atcatgagtt aattgaagct ctagattaca    10260
ttttcataac tgatgacata catctgacag gggagatttt tcatttttc agaagtttcg    10320 gccacccag acttgaagca gtaacggctg ctgaaaatgt taggaaatac atgaatcagc    10380
ctaaagtcat tgtgtatgag actctgatga aggtcatgc catatttgt ggaatcataa    10440 tcaacggcta tcgtgacagg cacgaggca gttggccacc gctgaccctc ccctgcatg    10500 ctgcagacac aatccggaat gctcaagctt caggtgaagg gttaacacat gagcagtgcg    10560
ttgataactg gagatctttt gctggagtga aatttggctg ctttatgcct cttagcctgg    10620
atagtgatct gacaatgtac ctaaaggaca aggcacttgc tgctctccaa agggaatggg    10680
attcagttta cccgaaagag ttcctgcgtt acgaccctcc caagggaacc gggtcacgga    10740
```

```
ggcttgtaga tgttttcctt aatgattcga gctttgaccc atatgatgtg ataatgtatg    10800
ttgtaagtgg agcttacctc catgaccctg agttcaacct gtcttacagc ctgaaagaaa    10860
aggagatcaa ggaaacaggt agacttttg ctaaaatgac ttacaaaatg agggcatgcc    10920
aagtgattgc tgaaaatcta atctcaaacg ggattggcaa atattttaag gacaatggga    10980
tggccaagga tgagcacgat ttgactaagg cactccacac tctagctgtc tcaggagtcc    11040
ccaaagatct caaagaaagt cacagggggg ggccagtctt aaaaacctac tcccgaagcc    11100
cagtccacac aagtaccagg aacgtgagag cagcaaaagg gtttataggg ttccctcaag    11160
taattcggca ggaccaagac actgatcatc cggagaatat ggaagcttac gagacagtca    11220
gtgcatttat cacgactgat ctcaagaagt actgccttaa ttggagatat gagaccatca    11280
gcttgtttgc acagaggcta aatgagattt acggattgcc ctcatttttc cagtggctgc    11340
ataagaggct tgagacctct gtcctgtatg taagtgaccc tcattgcccc cccgaccttg    11400
acgcccatat cccgttatat aaagtcccca atgatcaaat cttcattaag taccctatgg    11460
gaggtataga agggtattgt cagaagctgt ggaccatcag caccattccc tatctatacc    11520
tggctgctta tgagagcgga gtaaggattg cttcgttagt gcaaggggac aatcagacca    11580
tagccgtaac aaaaagggta cccagcacat ggccctacaa ccttaagaaa cgggaagctg    11640
ctagagtaac tagagattac tttgtaattc ttaggcaaag gctacatgat attggccatc    11700
acctcaaggc aaatgagaca attgtttcat cacatttttt tgtctattca aaaggaatat    11760
attatgatgg gctacttgtg tcccaatcac tcaagagcat cgcaagatgt gtattctggt    11820
cagagactat agttgatgaa acaagggcag catgcagtaa tattgctaca acaatggcta    11880
aaagcatcga gagaggttat gaccgttacc ttgcatattc cctgaacgtc ctaaaagtga    11940
tacagcaaat tctgatctct cttggcttca caatcaattc aaccatgacc cgggatgtag    12000
tcatacccct cctcacgaac aacgacctct aataaggat ggcactgttg cccgctccta    12060
ttgggggat gaattatctg aatatgagca ggctgtttgt cagaaacatc ggtgatccag    12120
taacatcatc aattgctgat ctcaagagaa tgattctcgc ctcactaatg cctgaagaga    12180
ccctccatca agtaatgaca caacaaccgg gggactcttc attcctagac tgggctagcg    12240
acccttactc agcaaatctt gtatgtgtcc agagcatcac tagactcctc aagaacataa    12300
ctgcaaggtt tgtcctgatc catagtccaa acccaatgtt aaaaggatta ttccatgatg    12360
acagtaaaga agaggacgag ggactggcgg cattcctcat ggacaggcat attatagtac    12420
ctagggcagc tcatgaaatc ctggatcata gtgtcacagg ggcaagagag tctattgcag    12480
gcatgctgga taccacaaaa ggcctgattc gagccagcat gaggaagggg gggttaacct    12540
ctcgagtgat aaccagattg tccaattatg actatgaaca attcagagca gggatggtgc    12600
tattgacagg aagaaagaga atgtcctca ttgacaaaga gtcatgttca gtgcagctgg    12660
cgagagctct aagaagccat atgtgggcga ggctagctcg aggacggcct atttacggcc    12720
ttgaggtccc tgatgtacta gaatctatgc gaggccacct tattcggcgt catgagacat    12780
gtgtcatctg cgagtgtgga tcagtcaact acggatggtt ttttgtcccc tcgggttgcc    12840
aactggatga tattgacaag gaaacatcat ccttgagagt cccatatatt ggttctacca    12900
ctgatgagag aacagacatg aagcttgcct tcgtaagagc cccaagtcga tccttgcgat    12960
ctgctgttag aatagcaaca gtgtactcat gggcttacgg tgatgatgat agctcttgga    13020
acgaagcctg gttgttggct aggcaaaggg ccaatgtgag cctggaggag ctaagggtga    13080
```

```
tcactcccat ctcaacttcg actaatttag cgcataggtt gagggatcgt agcactcaag    13140
tgaaatactc aggtacatcc cttgtccgag tggcgaggta taccacaatc tccaacgaca    13200
atctctcatt tgtcatatca gataagaagg ttgatactaa ctttatatac caacaaggaa    13260
tgcttctagg gttgggtgtt ttagaaacat tgtttcgact cgagaaagat accggatcat    13320
ctaacacggt attacatctt cacgtcgaaa cagattgttg cgtgatcccg atgatagatc    13380
atcccaggat acccagctcc cgcaagctag agctgagggc agagctatgt accaacccat    13440
tgatatatga taatgcacct ttaattgaca gagatacaac aaggctatac acccagagcc    13500
ataggaggca ccttgtggaa tttgttacat ggtccacacc ccaactatat cacattttag    13560
ctaagtccac agcactatct atgattgacc tggtaacaaa atttgagaag gaccatatga    13620
atgaaatttc agctctcata ggggatgacg atatcaatag tttcataact gagttttctgc   13680
tcatagagcc aagattattc actatctact tgggccagtg tgcggccatc aattgggcat    13740
ttgatgtaca ttatcataga ccatcaggga aatatcagat gggtgagctg ttgtcatcgt    13800
tcctttctag aatgagcaaa ggagtgttta aggtgcttgt caatgctcta agccacccaa    13860
agatctacaa gaaattctgg cattgtggta ttatagagcc tatccatggt ccttcacttg    13920
atgctcaaaa cttgcacaca actgtgtgca acatggttta cacatgctat atgacctacc    13980
tcgacctgtt gttgaatgaa gagttagaag agttcacatt tctcttgtgt gaaagcgacg    14040
aggatgtagt accggacaga ttcgacaaca tccaggcaaa acacttatgt gttctggcag    14100
atttgtactg tcaaccaggg acctgcccac caattcgagg tctaagaccg gtagagaaat    14160
gtgcagttct aaccgaccat atcaaggcag aggctaggtt atctccagca ggatcttcgt    14220
ggaacataaa tccaattatt gtagaccatt actcatgctc tctgacttat ctccggcgag    14280
gatcgatcaa acagataaga ttgagagttg atccaggatt cattttcgac gccctcgctg    14340
aggtaaatgt cagtcagcca agatcggca gcaacaacat ctcaaatatg agcatcaagg    14400
ctttcagacc cccacacgat gatgttgcaa aattgctcaa agatatcaac acaagcaagc    14460
acaatcttcc catttcaggg ggcaatctcg ccaattatga aatccatgct ttccgcagaa    14520
tcgggttgaa ctcatctgct tgctacaaag ctgttgagat atcaacatta attaggagat    14580
gccttgagcc aggggaggac ggcttgttct tgggtgaggg atcgggttcc atgttgatca    14640
cttataagga gatacttaaa ctaaacaagt gcttctataa tagtgggggtt tccgccaatt    14700
ctagatctgg tcaaagggaa ttagcaccct atccctccga agttggcctt gtcgaacaca    14760
gaatgggagt aggtaatatt gtcaaagtgc tctttaacgg gaggcccgaa gtcacgtggg    14820
taggcagtgt agattgcttc aatttcatag ttagtaatat ccctacctct agtgtggggt    14880
ttatccattc agatatagag accttgccta acaaagatac tatagagaag ctagaggaat    14940
tggcagccat cttatcgatg gctctgctcc tgggcaaaat aggatcaata ctggtgatta    15000
agcttatgcc tttcagcggg gattttgttc agggatttat aagttatgta gggtcccatt    15060
atagagaagt gaaccttgta taccctagat acagcaactt catatctact gaatcttatt    15120
tggttatgac agatctcaag gctaaccggc taatgaatcc tgaaaagatt aagcagcaga    15180
taattgaatc atctgtgagg acttcacctg gacttatagg tcacatccta tccattaagc    15240
aactaagctg catacaagca attgtgggag acgcagttag tagaggtgat atcaatccta    15300
ctctgaaaaa acttacacct atagagcagg tgctgatcaa ttgcgggttg gcaattaacg    15360
gacctaagct gtgcaaagaa ttgatccacc atgatgttgc ctcagggcaa gatgattgc    15420
ttaattctat actcatcctc tacagggagt tggcaagatt caaagacaac caaagaagtc    15480
```

```
aacaagggat gttccacgct taccccgtat tggtaagtag caggcaacga gaacttatat    15540
ctaggatcac ccgcaaattt tgggggcaca ttcttcttta ctccgggaac agaaagttga    15600
taaataagtt tatccagaat ctcaagtccg gctatctgat actagactta caccagaata    15660
tcttcgttaa gaatctatcc aagtcagaga aacagattat tatgacgggg ggtttgaaac    15720
gtgagtgggt ttttaaggta acagtcaagg agaccaaaga atggtataag ttagtcggat    15780
acagtgccct gattaaggac taagcggcc                                     15809
```

<210> SEQ ID NO 10
<211> LENGTH: 15
<212> TYPE: DNA
<213> ORGANISM: artificial sequence
<220> FEATURE:
<223> OTHER INFORMATION: primer for synthesis of cDNA of entire MV-E
      genome <400> SEQUENCE: 10
gcggccgcac caaac                                                    15

<210> SEQ ID NO 11
<211> LENGTH: 15
<212> TYPE: DNA
<213> ORGANISM: artificial sequence
<220> FEATURE:
<223> OTHER INFORMATION: primer for synthesis of cDNA of entire MV-E
      genome <400> SEQUENCE: 11
cctgaccgcg gatgc                                                    15

<210> SEQ ID NO 12
<211> LENGTH: 15
<212> TYPE: DNA
<213> ORGANISM: artificial sequence
<220> FEATURE:
<223> OTHER INFORMATION: primer for synthesis of cDNA of entire MV-E
      genome <400> SEQUENCE: 12
acctcgcatc cgcgg                                                    15

<210> SEQ ID NO 13
<211> LENGTH: 22
<212> TYPE: DNA
<213> ORGANISM: artificial sequence
<220> FEATURE:
<223> OTHER INFORMATION: primer for synthesis of cDNA of entire MV-E
      genome <400> SEQUENCE: 13
cctccagagt aatcgattaa gg                                            22

<210> SEQ ID NO 14
<211> LENGTH: 23
<212> TYPE: DNA
<213> ORGANISM: artificial sequence
<220> FEATURE:
<223> OTHER INFORMATION: primer for synthesis of cDNA of entire MV-E
      genome <400> SEQUENCE: 14
aatcgattac tctggaggag cag                                           23

<210> SEQ ID NO 15
<211> LENGTH: 27
<212> TYPE: DNA
<213> ORGANISM: artificial sequence
<220> FEATURE:
<223> OTHER INFORMATION: primer for synthesis of cDNA of entire MV-E genome

<400> SEQUENCE: 15
cttgcaccct aagttttaat taactac        27

<210> SEQ ID NO 16

```
<211> LENGTH: 22
<212> TYPE: DNA
<213> ORGANISM: artificial sequence
<220> FEATURE:
<223> OTHER INFORMATION: primer for synthesis of cDNA of entire MV-E
      genome

<400> SEQUENCE: 21
gagcatcaag tgaaggacca tg                                            22

<210> SEQ ID NO 22
<211> LENG

<212> TYPE: DNA
<213> ORGANISM: artificial sequence
<220> FEATURE:
<223> OTHER INFORMATION: Reverse (P) random hexamer for RNA preparation
      from purified MV-E virus

<400> SEQUENCE: 27
gcggccgcct acttcattat tatc                                           24

<210> SEQ ID NO 28
<211> LENGTH: 27
<212> TYPE: DNA
<213> ORGANISM: artificial sequence
<220> FEATURE:
<223> OTHER INFORMATION: Forward (L) random hexamer for RNA preparation
      from purified MV-E virus

<400> SEQUENCE: 28
gctagcatgg actcgctatc tgtcaac                                        27

<210> SEQ ID NO 29
<211> LENGTH: 23
<212> TYPE: DNA
<213> ORGANISM: artificial sequence
<220> FEATURE:
<223> OTHER INFORMATION: Reverse (L) random hexamer for RNA preparation
      from purified MV-E virus

<400> SEQUENCE: 29
gcggccgctt agtccttaat cag                                            23

<210> SEQ ID NO 30
<211> LENGTH: 130
<212> TYPE: DNA
<213> ORGANISM: artificial sequence
<220> FEATURE:
<223> OTHER INFORMATION: pentameric IRES elememt flanked by a site for
      EagI at 5' and first 10 nucleotides of L protein at 3'

<400> SEQUENCE: 30
ggccgttctg acatccggcg ggtttctgac atccggcggg tttctgacat ccggcgggtt    60
tctgacatcc ggcgggtttc tgacatccgg cgggtgactc acaacggatc caacagacat   120
atggactcgc                                                          130

<210> SEQ ID NO 31
<211> LENGTH: 91
<212> TYPE: DNA
<213> ORGANISM: artificial sequence
<220> FEATURE:
<223> OTHER INFORMATION: porcine teschovirus 2A peptide flanked on the
      5'end by the codons immediately before stop codon of MV N protein
      and on the 3'end by the first few codons of MV P protein

<400> SEQUENCE: 31
atcttctaga cggctccgga gccacgaact tctctctgtt aaagcaagca ggagacgtgg    60
aagaaaaccc cggtcccatg gcagaagagc a                                   91

The invention claimed is:

1. A two plasmid system for producing recombinant proteins using RNA dependent RNA Polymerase of non-segmented negative strand RNA viruses comprising:
   a. one cloning plasmid that expresses the recombinant proteins, comprising a manipulatable replicon having at least two multiple cloning sites for inserting genes encoding the recombinant proteins, and
   b. one helper plasmid that expresses N, P, and L proteins, comprising N, P, and L genes expressing the N, P, and L proteins, respectively;
   without the help of a helper vaccinia virus or exogenous RNA polymerase, wherein the manipulatable replicon sequence is as set forth in SEQ ID NO: 1.

2. The two plasmid system as claimed in claim 1, wherein the helper plasmid is selected from the group consisting of SEQ ID NO: 8, and SEQ ID NO: 9.

3. The two plasmid system as claimed in claim 1, wherein the cloning plasmid is selected from the group consisting of SEQ ID NO: 4, SEQ ID NO: 5, SEQ ID NO: 6, and SEQ ID NO: 7.

4. A two plasmid system for producing recombinant proteins using RNA dependent RNA Polymerase of non-segmented negative strand RNA viruses comprising:
   a. one cloning plasmid that expresses the recombinant proteins, comprising a manipulatable replicon having at least two multiple cloning sites for inserting genes encoding the recombinant proteins, and
   b. one helper plasmid that expresses N, P, and L proteins, comprising N, P, and L genes expressing the N, P, and L proteins, respectively;
   without the help of a helper vaccinia virus or exogenous RNA polymerase, wherein the manipulatable replicon is flanked by ribozymes, and said manipulatable replicon sequence is as set forth in SEQ ID NO: 2.

5. The two plasmid system as claimed in claim 4, wherein the helper plasmid is selected from the group consisting of SEQ ID NO: 8, and SEQ ID NO: 9.

6. The two plasmid system as claimed in claim 4, wherein the cloning plasmid is selected from the group consisting of SEQ ID NO: 4, and SEQ ID NO: 7.

7. A two plasmid system for producing recombinant proteins using RNA dependent RNA Polymerase of non-segmented negative strand RNA viruses comprising:
   a. one cloning plasmid that expresses the recombinant proteins, comprising a manipulatable replicon having at least two multiple cloning sites for inserting genes encoding the recombinant proteins, and
   b. one helper plasmid that expresses N, P, and L proteins, comprising N, P, and L genes expressing the N, P, and L proteins, respectively;
   without the help of a helper vaccinia virus or exogenous RNA polymerase, wherein the manipulatable replicon is flanked by RNA polymerase I promoter and RNA polymerase I terminator, and said manipulatable replicon sequence is as set forth in SEQ ID NO: 3.

8. The two plasmid system as claimed in claim 7, wherein the helper plasmid is selected from the group consisting of SEQ ID NO: 8, and SEQ ID NO: 9.

9. The two plasmid system as claimed in claim 7, wherein the cloning plasmid is selected from the group consisting of SEQ ID NO: 5, and SEQ ID NO: 6.

* * * * *